US011154391B2

(12) United States Patent
Ponsky et al.

(10) Patent No.: US 11,154,391 B2
(45) Date of Patent: Oct. 26, 2021

(54) URETERAL STENT FOR PLACEMENT IN A KIDNEY AND BLADDER

(71) Applicant: UNIVERSITY HOSPITALS HEALTH SYSTEMS, INC., Cleveland, OH (US)

(72) Inventors: Lee E. Ponsky, Moreland Hills, OH (US); Dean Secrest, Concord, OH (US)

(73) Assignee: UNIVERSITY HOSPITALS HEALTH SYSTEMS, INC., Cleveland, OH (US)

( * ) Notice: Subject to any disclaimer, the term of this patent is extended or adjusted under 35 U.S.C. 154(b) by 378 days.

(21) Appl. No.: 15/192,314

(22) Filed: Jun. 24, 2016

(65) Prior Publication Data

US 2017/0319324 A1 Nov. 9, 2017

Related U.S. Application Data

(63) Continuation-in-part of application No. PCT/US2016/031104, filed on May 6, 2016.

(51) Int. Cl.
*A61F 2/04* (2013.01)

(52) U.S. Cl.
CPC ............... *A61F 2/04* (2013.01); *A61F 2/042* (2013.01); *A61F 2002/047* (2013.01); *A61F 2230/0069* (2013.01)

(58) Field of Classification Search
CPC .... A61F 2/04; A61F 2/044; A61F 2/82; A61F 2/95; A61F 2230/0069; A61F 2002/047; A61F 2/042; A61M 27/008
See application file for complete search history.

(56) References Cited

U.S. PATENT DOCUMENTS 3,995,642 A 12/1976 Adair
4,787,884 A 11/1988 Goldberg
(Continued)

FOREIGN PATENT DOCUMENTS

DE 4103573 8/1992
DE 4134030 4/1993
(Continued)

OTHER PUBLICATIONS

International Search Report with the Written Opinion in PCT/US2016/031104, dated Mar. 13, 2017.

*Primary Examiner* — Jacqueline Woznicki
(74) *Attorney, Agent, or Firm* — Tucker Ellis LLP

(57) ABSTRACT

Provided is a ureteral stent for placement in a bladder, a kidney and a ureteral passageway connecting the bladder and the kidney. The ureteral stent includes a solid bladder portion free of a lumen positionable in the bladder, a tubular kidney portion positionable in the kidney and the ureteral passageway, and a tether connecting the bladder portion and the ureter portion to allow the bladder portion to float in the bladder and to allow a ureter orifice connecting the ureteral passageway to the bladder to move between a compressed state and an uncompressed state. By not having a lumen, the solid bladder portion allows the bladder to have a smaller diameter while maintaining a necessary uncoil force. The smaller diameter also allows the bladder portion to be inserted into a scope alongside a pusher tube, thereby avoiding loading the bladder portion onto a guidewire.

12 Claims, 25 Drawing Sheets

(56) References Cited

U.S. PATENT DOCUMENTS

| | | | |
|---|---|---|---|
| 4,790,809 A | 12/1988 | Kuntz | |
| 4,874,360 A | 10/1989 | Goldberg | |
| 4,913,683 A | 4/1990 | Gregory | |
| 4,931,037 A | 6/1990 | Wetterman | |
| 5,141,502 A | 8/1992 | Macaluso | |
| 5,322,501 A | 6/1994 | Mahmud-Durrani | |
| 5,456,246 A | 10/1995 | Schmieding | |
| 5,599,291 A | 2/1997 | Balbierz | |
| 6,258,098 B1 | 7/2001 | Taylor | |
| 6,652,569 B1 * | 11/2003 | Taylor | A61F 2/04 606/108 |
| 6,656,146 B1 | 12/2003 | Clayman | |
| 6,852,105 B2 | 2/2005 | Bolmsjoet | |
| 7,041,139 B2 | 5/2006 | Bluni | |
| 8,070,825 B2 | 12/2011 | Devonec | |
| 8,474,814 B2 | 7/2013 | Noda | |
| 9,492,266 B2 | 11/2016 | Hutchins | |
| 2002/0143389 A1 | 10/2002 | St. Pierre | |
| 2003/0109930 A1 * | 6/2003 | Bluni | A61F 2/04 623/23.7 |
| 2003/0153973 A1 | 8/2003 | Soun | |
| 2003/0176912 A1 | 8/2003 | Chuter | |
| 2003/0181842 A1 | 9/2003 | Gellman | |
| 2004/0059279 A1 * | 3/2004 | McWeeney | A61M 27/008 604/8 |
| 2004/0167635 A1 * | 8/2004 | Yachia | A61F 2/90 623/23.66 |
| 2005/0149201 A1 | 7/2005 | McWeeney | |
| 2006/0052815 A1 | 3/2006 | Fitz | |
| 2007/0293929 A1 | 12/2007 | Aoba | |
| 2008/0004578 A1 | 1/2008 | Hixon | |
| 2008/0077250 A1 | 3/2008 | Amos | |
| 2008/0183299 A1 | 7/2008 | Monga | |
| 2008/0255678 A1 * | 10/2008 | Cully | A61F 5/0076 623/23.65 |
| 2009/0163780 A1 | 6/2009 | Tieu | |
| 2010/0070024 A1 | 3/2010 | Venturelli | |
| 2010/0152861 A1 * | 6/2010 | Chung | A61M 27/008 623/23.7 |
| 2010/0160848 A1 | 6/2010 | Ostrovsky | |
| 2010/0324540 A1 | 12/2010 | Paulen | |
| 2011/0320008 A1 | 12/2011 | Teague | |
| 2012/0158155 A1 | 6/2012 | Shin | |
| 2012/0303109 A1 | 11/2012 | Okuma | |
| 2013/0158675 A1 | 6/2013 | Hutchins | |
| 2015/0005893 A1 | 1/2015 | Harrah | |
| 2015/0142127 A1 | 5/2015 | Ponsky | |
| 2016/0128852 A1 * | 5/2016 | Leanna | A61F 2/89 623/9 |

FOREIGN PATENT DOCUMENTS

| | | | |
|---|---|---|---|
| FR | 2577809 | 8/1986 | |
| GB | WO 2005096991 A1 * | 10/2005 | A61F 2/04 |
| WO | 2005096991 | 10/2005 | |
| WO | 2005102217 | 11/2005 | |
| WO | 2007001978 | 1/2007 | |
| WO | WO2013185133 | 12/2013 | |

* cited by examiner

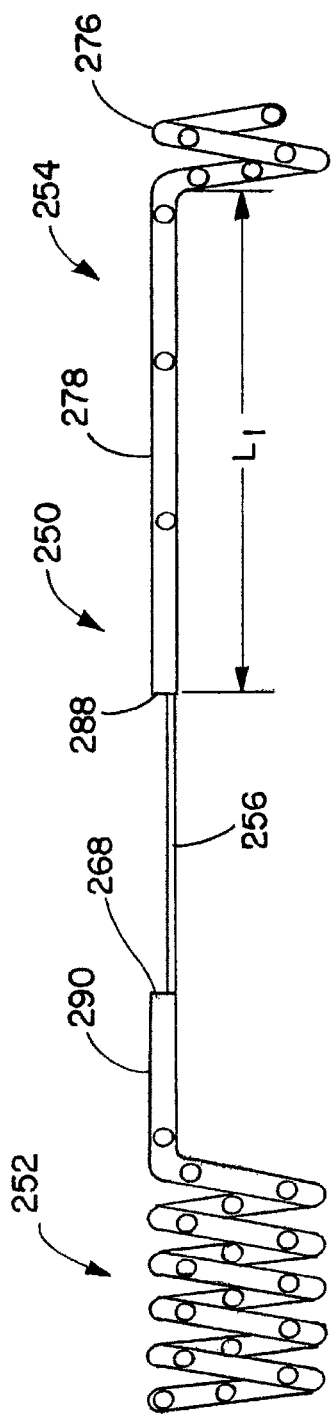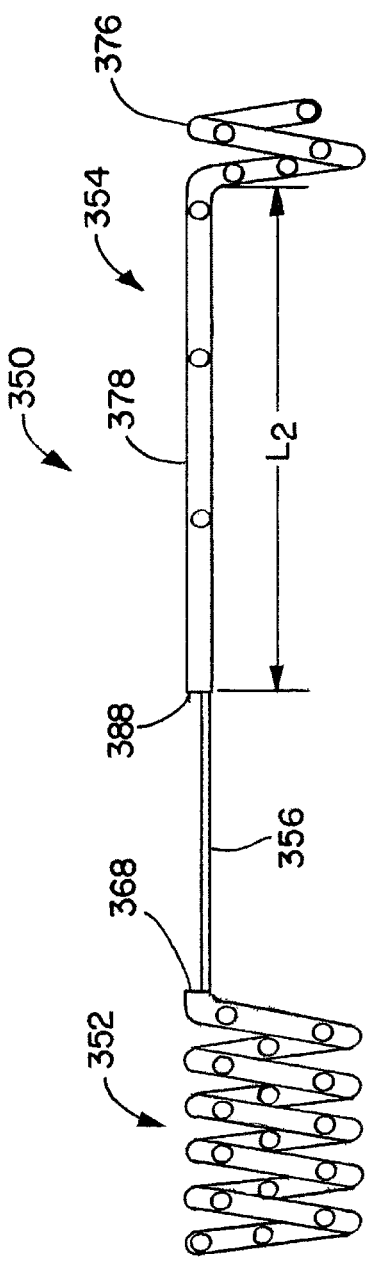

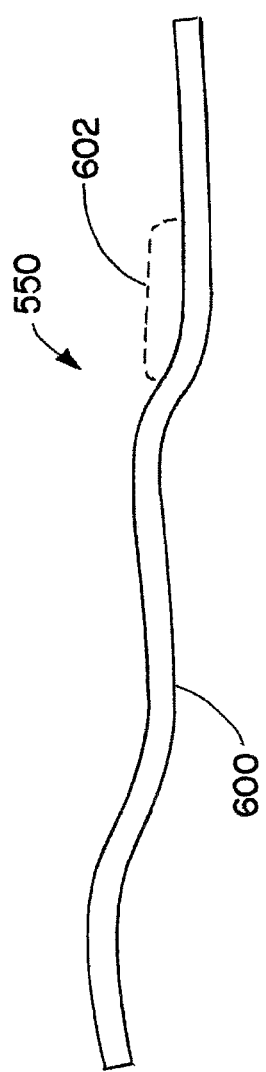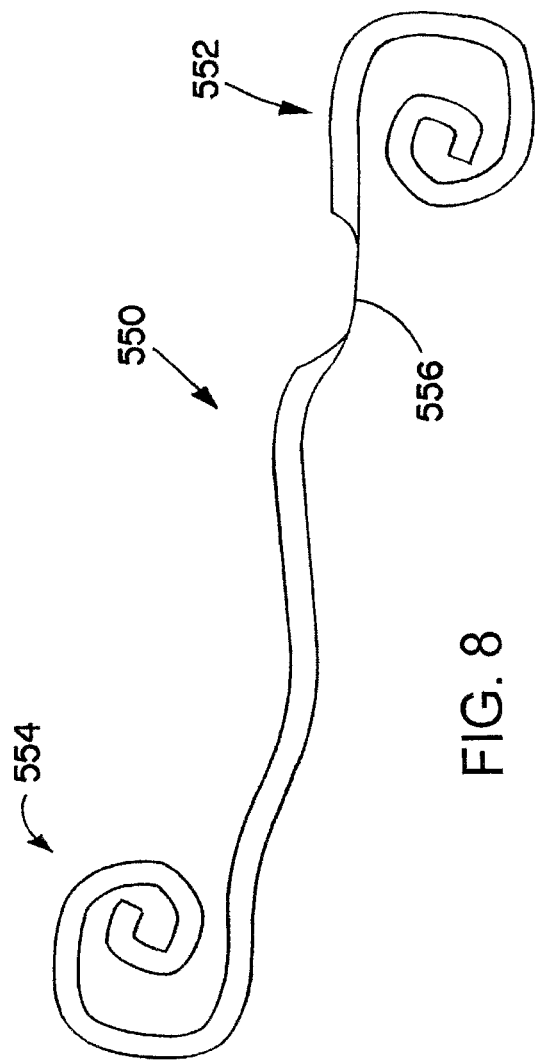
FIG. 7
FIG. 8

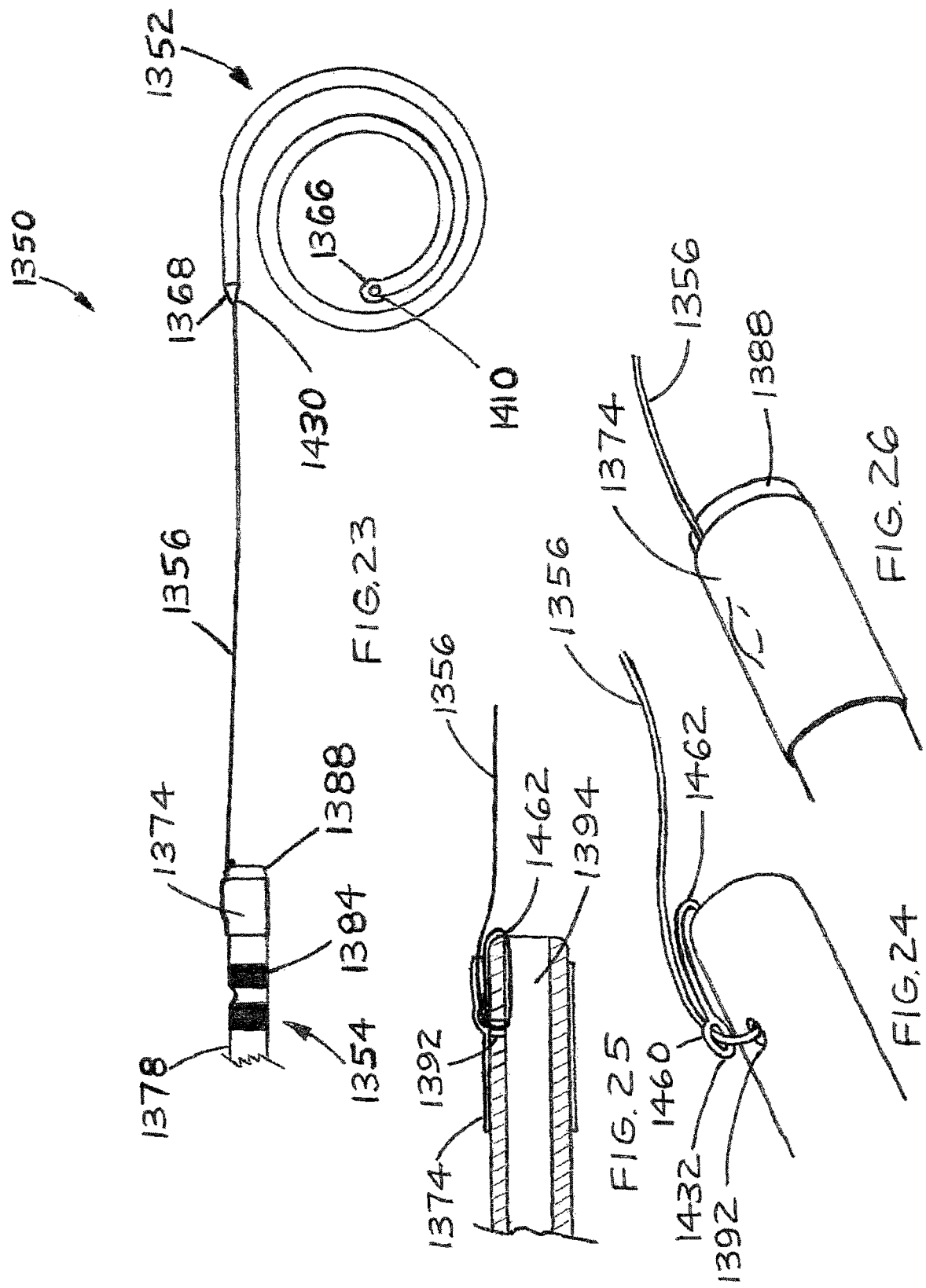

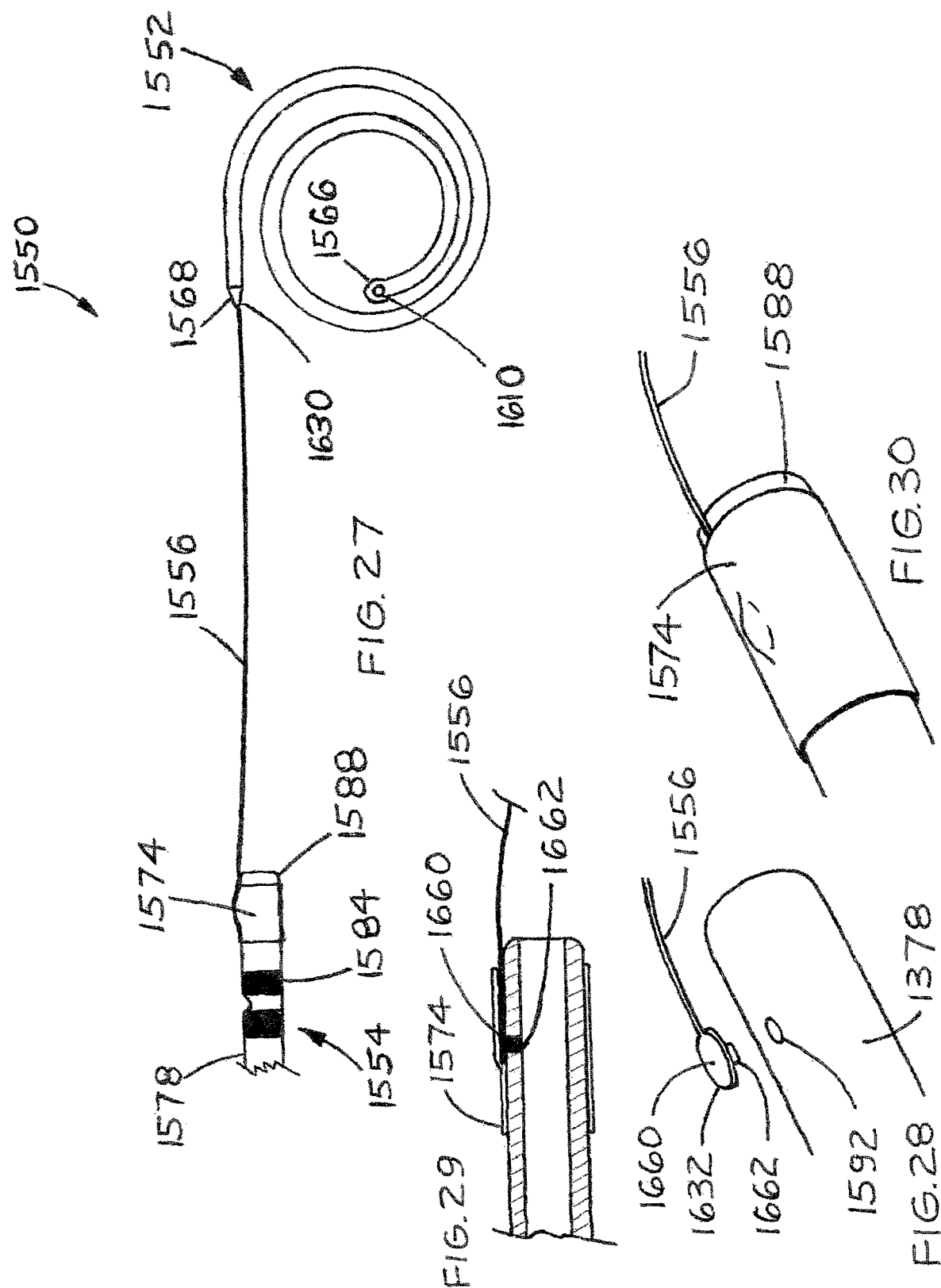

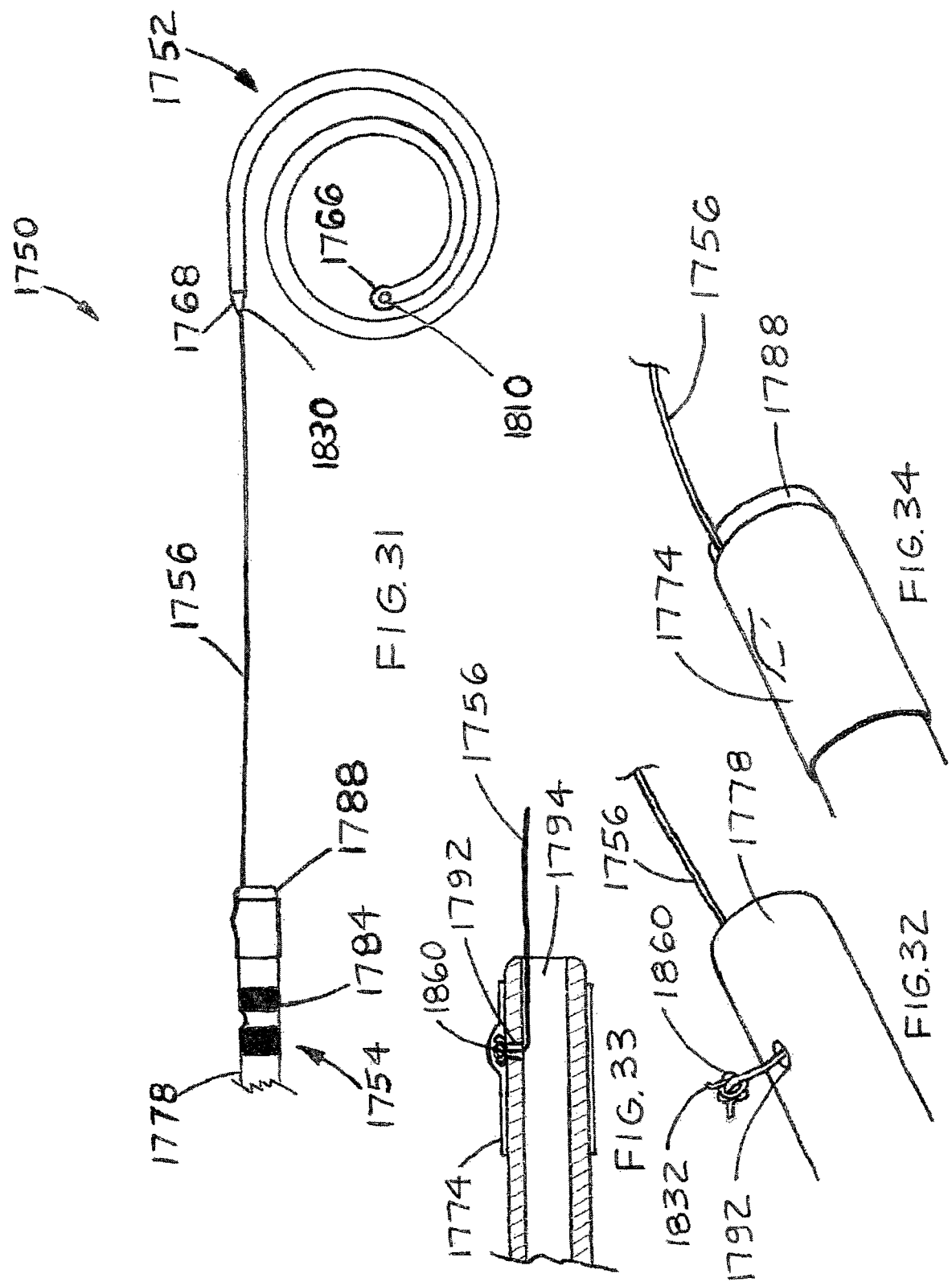

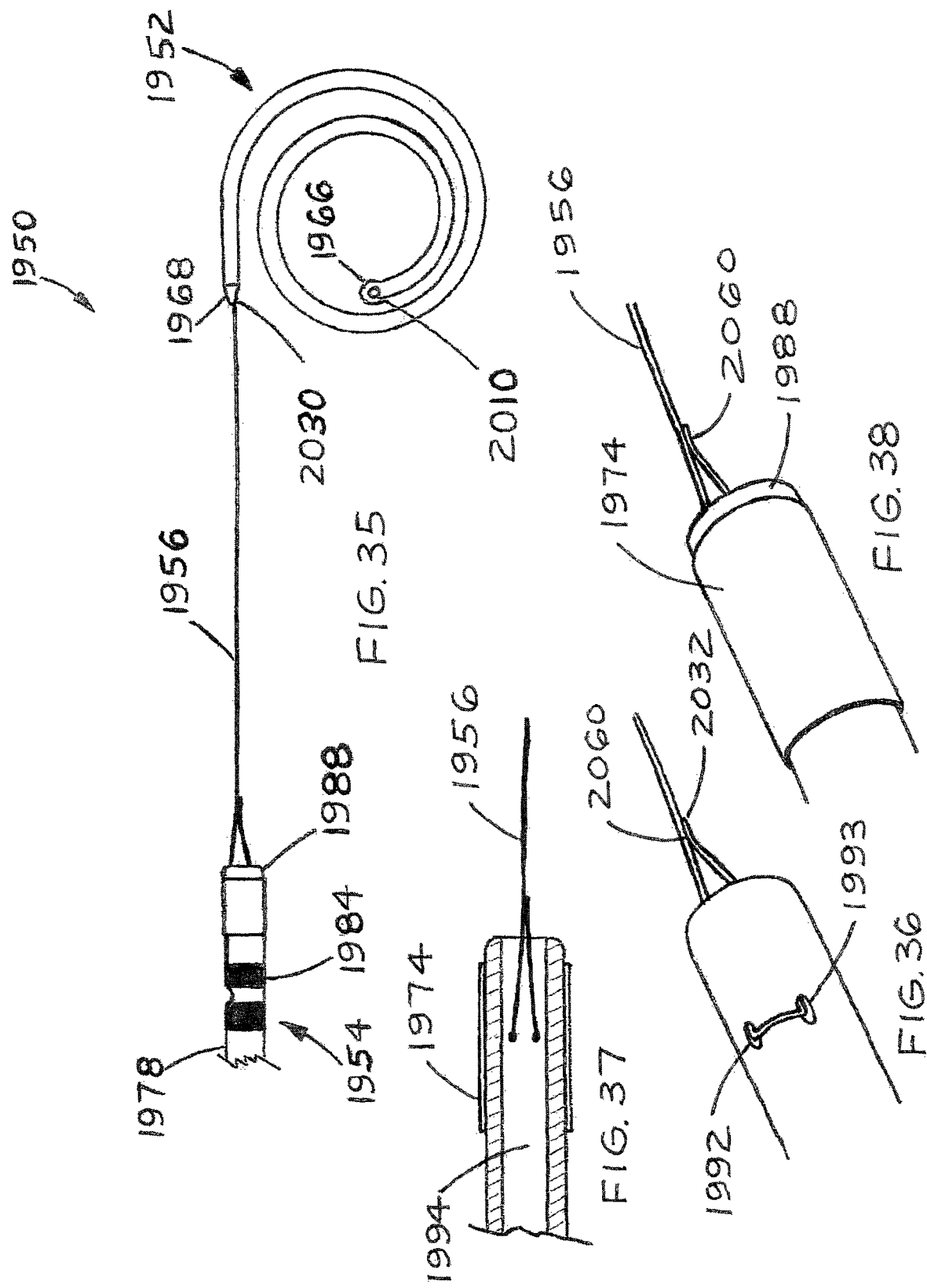

URETERAL STENT FOR PLACEMENT IN A
KIDNEY AND BLADDER

RELATED APPLICATIONS

This application is a continuation-in-part of International Application No. PCT/US2016/031104 filed May 6, 2016, which is hereby incorporated herein by reference.

FIELD OF INVENTION

The present invention relates generally to implantable medical devices, and more particularly to stents, such as ureteral stents.

BACKGROUND

The urinary tract has a pair of kidneys that connect to a bladder by ureteral passageways, and a urethra that extends from the bladder to the exterior of a patient. Urine is made by the kidneys, passed through the ureteral passageway, stored in the bladder and ultimately voided from the urethra. A urinary sphincter is positioned around the urethra near the base of the bladder to control the flow of urine from the bladder.

The ureteral passageways normally allow urine to pass from the kidney to the bladder by peristalsis. When the bladder fills with urine, the bladder compresses a segment of the ureteral passageway that passes through a wall of the bladder to prevent urine from going backwards from the bladder into the kidney. These passageways can become blocked by tumors, scar tissue or kidney stones thereby preventing normal urine flow, and the resulting high pressure within the kidneys can cause pain to the patient. To reopen a blocked ureteral passageway, a ureteral stent can be positioned in the patient. The stent holds the blockage in the passageway open, and allows the urine to bypass the blockage. This enables urine to flow from the kidney into the bladder, reduces kidney pressure, and reduces pain of the patient.

SUMMARY OF INVENTION

Provided is a ureteral stent for placement in a bladder, a kidney and a ureteral passageway connecting the bladder and the kidney. The ureteral stent includes a solid bladder portion free of a lumen positionable in the bladder, a tubular kidney portion positionable in the kidney and the ureteral passageway, and a tether connecting the bladder portion and the ureter portion to allow the bladder portion to float in the bladder and to allow a ureter orifice connecting the ureteral passageway to the bladder to move between a compressed state and an uncompressed state. By not having a lumen, the solid bladder portion allows the bladder to have a smaller diameter while maintaining a necessary uncoil force. The smaller diameter also allows the bladder portion to be inserted into a scope alongside a pusher tube, thereby avoiding loading the bladder portion onto a guidewire and simplifying the delivery process for the physician.

The foregoing and other features of the application are described below with reference to the drawings.

BRIEF DESCRIPTION OF THE DRAWINGS

FIG. 4 is a schematic view of yet another exemplary stent.
FIG. 5 is a schematic view of still another exemplary stent.
FIGS. 7 and 8 are schematic views of still a further exemplary stent.
FIG. 23 is a partial side view of another exemplary stent.
FIG. 24 is a partial perspective view of the stent of FIG. 23.
FIG. 25 is a partial cross-sectional view of the stent of FIG. 23.
FIG. 26 is another partial perspective view of the stent of FIG. 23.
FIG. 27 is a partial side view of still another exemplary stent.
FIG. 28 is a partial perspective view of the stent of FIG. 27.
FIG. 29 is a partial cross-sectional view of the stent of FIG. 27.
FIG. 30 is another partial perspective view of the stent of FIG. 27.
FIG. 31 is a partial side view of yet another exemplary stent.
FIG. 32 is a partial perspective view of the stent of FIG. 31.
FIG. 33 is a partial cross-sectional view of the stent of FIG. 31.
FIG. 34 is another partial perspective view of the stent of FIG. 31.
FIG. 35 is a partial side view of a further exemplary stent.
FIG. 36 is a partial perspective view of the stent of FIG. 35.
FIG. 37 is a partial cross-sectional view of the stent of FIG. 35.
FIG. 38 is another partial perspective view of the stent of FIG. 35.

DETAILED DESCRIPTION

The principles of the present application have particular application to ureteral stents for unblocking a ureteral passageway and thus will be described below chiefly in this context. It will, of course, be appreciated and also understood that the principles of the application may be useful in other medical applications, such as other stent applications, for example biliary stents.

Figure 1:
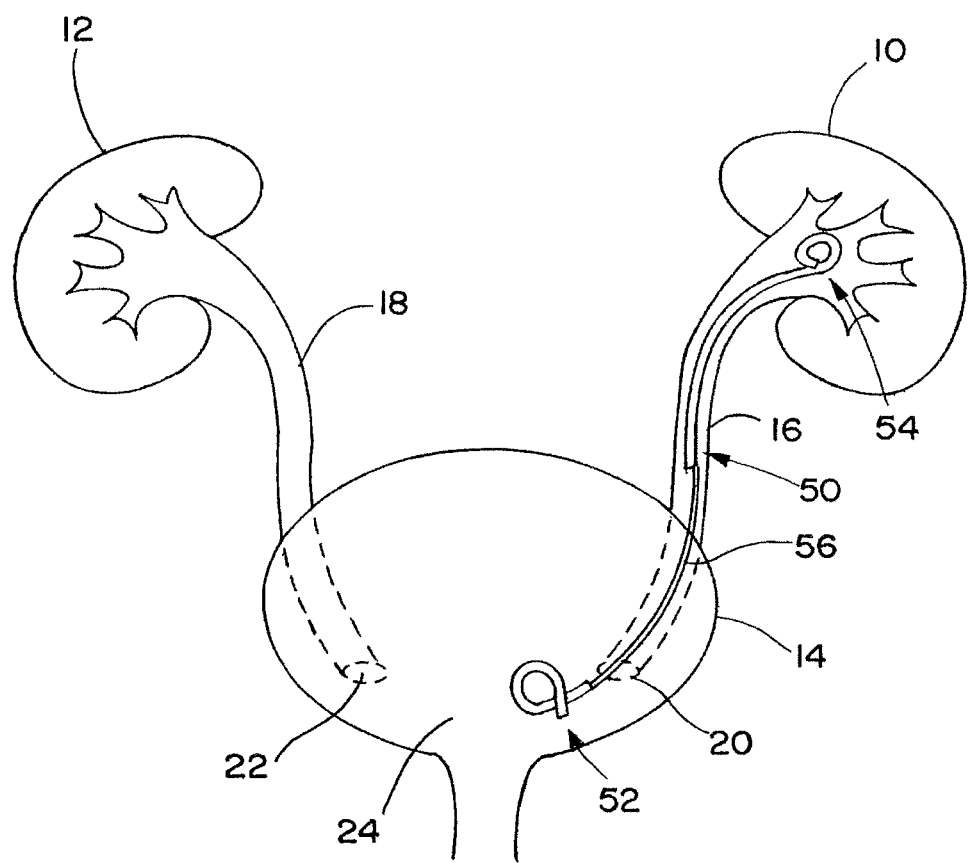
FIG. 1 is a schematic view of an exemplary stent positioned in a patient.

Referring now in detail to the drawings and initially to FIG. 1, a pair of kidneys 10 and 12 and a bladder 14 of a patient are shown. The kidneys 10 and 12 are connected to the bladder 14 by respective ureteral passageways 16 and 18. The ureteral passageways 16 and 18 each include a portion extending into the bladder 14 that moves from an uncompressed state to compressed state and in a normal state only allows urine to pass from the kidneys 10 and 12 to the bladder 14 with the help of peristalsis of the ureter. When one of the passageways 16 and 18 becomes blocked, for example by blockage from a kidney or ureteral stone, a ureteral stent may be positioned in the kidney 10, 12, ureteral passageway 16, 18 and bladder 14 to assist in opening the passageway 16, 18 to aid in the flow of urine.

The ureteral stent may be formed by a tube extending from the kidney 10, 12 to the bladder 14, the tube having a first helical end positioned in the kidney and a second helical end positioned in the bladder. Although such a stent allows urine to flow through and around the tube into the bladder, the tube may cause or contribute to patient discomfort and further medical problems. For example, the tube causes ureter orifices 20 and 22, which normally move from a compressed state to an uncompressed state, to remain open at all times allowing urine to flow from the bladder 14 to the kidney 10, 12 and the kidney 10, 12 to the bladder 14. Keeping the ureter orifices 20 and 22 open, thereby preventing the orifices 20 and 22 from compressing to prevent urine from flowing from the bladder 14 to the kidneys 10 and 12, may lead to urinary reflux and flank pain, for example. The bladder end of the ureteral stent also typically rests on or contacts a trigone 24 of the patient or wall of the bladder 14, causing blood in the urine, an intermittent strong urge to urinate, and painful bladder spasms resulting from the stent and therefore increased discomfort of the patient.

Figure 2:
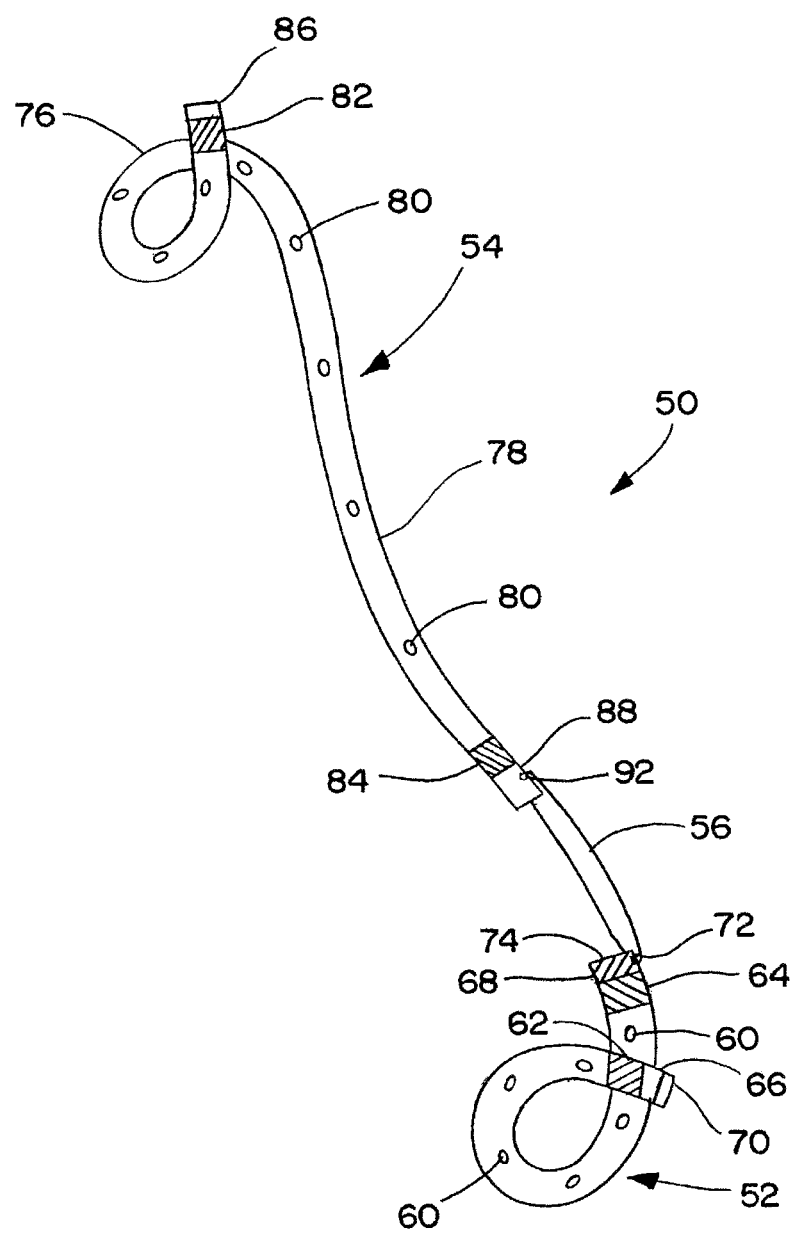
FIG. 2 is a schematic view of the stent of FIG. 1.

To minimize the footprint of the stent in the bladder 14 and/or near the ureteral orifices 20 and 22 and to allow urine to flow in a single direction from the kidneys 10 and 12 to the bladder 14 and not from the bladder 14 to the kidneys 10 and 12, thereby reducing the adverse effects associated with stents, an exemplary ureteral stent 50 is provided. As shown in FIGS. 1 and 2, the stent 50 includes a bladder portion 52 positioned in the bladder 14, a kidney portion 54 positioned in the kidney 10 and ureteral passageway 16, and one or more tethers 56 coupling the bladder portion 52 to the kidney portion 54. The tether 56 may be a suitable thread, which is not limited to fibers, and may include, for example, a wire, such as a thin wire. Although not shown, it will be appreciated that the stent 50 may additionally or alternatively be positioned in the kidney 12 and ureteral passageway 18.

The bladder portion 52 is a resilient fixing member having any suitable shape, such as a tube that is curved in a flexible loop as shown in FIG. 2 when unrestrained to prevent the bladder portion 52 from migrating into the ureteral passageway 16. The bladder portion 52 is in an unrestrained shape when positioned in the bladder 14, and in a restrained shape, such as a substantially straight shape, when being positioned in the bladder 14. It will be appreciated that the bladder portion may be any suitable shape when unrestrained, such as J-shaped (FIG. 3), helical (FIGS. 4 and 5), t-bar (FIG. 6), triangular (FIG. 9), circular (FIG. 10), etc. It will also be appreciated that the bladder portion may be made of any suitable material that does not irritate the patient's ureter tissue, such as urethane polymer, silicone, a thermoplastic, for example a thermoplastic polymer or elastomer, etc. It will also be appreciated that the suitable material may be a buoyant material to allow the bladder portion to float in the bladder, for example when the bladder is filled with urine, to allow the bladder portion to float off the trigone thereby decreasing irritation.

The bladder portion 52 may include one or more openings 60 in a wall of the bladder portion that allow fluid to flow in/out of the bladder portion. The openings may be any suitable shape and size, such as a spiral, a circular opening, etc. The bladder portion 52 may also include at least one radiopaque element, such as a radiopaque band, and in the illustrated embodiment radiopaque bands 62 and 64 near first and second ends 66 and 68 of the bladder portion, respectively. The radiopaque bands may be any suitable radiopaque element provided to assist an operator in placing the stent 50. Additionally or alternatively, it will be appreciated that the bladder portion 52 may be radiopaque to assist in positioning the stent. The bladder portion may also include a tip or ring 70 at the first end 66 having a stiffness greater than a stiffness of the rest of the bladder portion 52 to assist in the positioning of the stent 50.

Similar to the bladder portion 52, the kidney portion 54 has a resilient fixing portion 76, such as a tube in the form of a flexible loop when unrestrained to secure the kidney portion in the kidney 10. The resilient fixing portion 76 is in an unrestrained shape when positioned in the kidney, and in a restrained shape, such as a substantially straight shape, when being positioned in the kidney. It will be appreciated that the fixing portion may be any suitable shape when unrestrained, such as J-shaped (FIG. 3), helical (FIGS. 4 and 5), etc. It will also be appreciated that the bladder portion 52 and kidney portion 54 may have the same or different shapes when unrestrained, for example the bladder portion 52 and kidney portion 54 may both be a flexible loop as shown in FIG. 2, the bladder portion 52 or kidney portion 54 may be J-shaped and the other portion may be helical, etc.

The kidney portion 54 may be made of any suitable material that does not irritate the patient's ureter tissue, such as urethane polymer, silicone, a thermoplastic, for example a thermoplastic polymer or elastomer, etc. It will be appreciated that the kidney portion and bladder portion may be made of the same or different materials having the same or different durometers that are sufficient to allow for delivery reliability during placement while having tensile properties allowing for removal from the body. The kidney portion may have a durometer, for example, of 50 to 80 shore A and preferably 50 to 60 shore A, and the bladder portion may have a durometer, for example, of 25 to 50 shore A, and preferably 30 to 40 shore A. It will also be appreciated that the kidney portion, bladder portion, and/or tether may be made of one or more of an absorbable or non-absorbable material, a material to prevent calcification, a material to prevent incrustation, and may additionally or alternatively be impregnated with a suitable antibiotic and/or be drug-eluting.

In an embodiment, the bladder portion 52 has a softer durometer than the kidney portion 54 so that the bladder portion 52 is compliant with bladder contractions and to reduce irritation to the trigone 24. Additionally or alternatively, the resilient fixing portion 76 of the kidney portion 54 is harder than a ureter portion 78 of the kidney portion 54. For example, the kidney portion 54 may have transition zones along its length going from a harder durometer at the fixing portion 76 to a softer durometer at the end of the ureter portion 78. It will also be appreciated that the bladder portion 52 and/or kidney portion 54 may be heat activated such that the portions are stiffer during placement and soften after placement in the body.

Referring again to the kidney portion 54, the kidney portion has the ureter portion 78, which may be a flexible tubular portion, configured to extend from the resilient fixing portion 76 in the kidney 10 into the ureteral passageway 16 to keep the passageway open, for example when there is a blockage between the kidney 10 and passageway 16. The kidney portion 54 may also include one or more openings 80 in a wall of the kidney portion 54 that allow fluid to flow in/out of the kidney portion 54. The openings may be any suitable shape and size, such as a spiral (FIG. 3), a circular opening, etc.

The kidney portion 54 also includes at least one radiopaque element, such as a radiopaque band, and in the illustrated embodiment radiopaque bands 82 and 84 near first and second ends 86 and 88 of the kidney portion 54, respectively, although it will be appreciated that the kidney portion 54 may additionally or alternatively be radiopaque to assist in placing the stent and identifying the stent on x-rays during placing. It will also be appreciated that the bladder portion 52 and/or kidney portion 54 may include measurement markers along their respective lengths to assist in positioning the stent 50.

As noted above, the bladder portion 52 and kidney portion 54 are coupled together by one or more tethers 56. The tethers 56 have a thin flexible cross-section such that a transmural portion of the ureteral passageway, which passes through the bladder wall starting at the ureter opening and continuing through the thickness of the bladder 14, can clamp or remain in its normal state around the tethers 56. This allows for the single direction of urine flow from the kidney 10 to the bladder 14 to be maintained and prevents the flow or reflux of urine from the bladder 14 to the kidney 10. The tethers 56 may be any suitable tether having any suitable cross-sectional shape, such as a suitable suture made of cotton, a polymer such as nylon, etc. The tethers may also be any suitable length. For example, the tethers may be uniform in length for patients of varying sizes and the ureter portion 78 may be altered in length to accommodate patients of varying sizes and/or the suture lengths may be varied for patients of varying sizes. It will also be appreciated that the one or more tethers 56 may include one or more radiopaque marks along their lengths.

The tethers 56 are coupled to the second end 68 of the bladder portion and the second end 88 of the kidney portion in any suitable manner, for example by adhesive, knotting, etc. For example, as shown in FIG. 2, the tether 56 has an end received in an opening 92 at the second end 88 of the kidney portion 54 such that a portion of the tether 56 is outside the kidney portion 54 and a portion is inside the kidney portion 54. The portion of the tether 56 inside the kidney portion 54 extends to an inside of the bladder portion 52, where the tether extends out of an opening 72 in the bladder portion 52. Ends of the tether 56 are coupled together outside the bladder portion or the kidney portion, for example by tying the two ends together forming a knot. The excess tether created by the tying may then be cut off.

In an embodiment, a sleeve 74, such as a heat shrink, tape, UV adhesive, etc., is coupled to the second end 68 of the bladder portion to hold down the knot and excess tether to prevent or minimize irritation to the patient. It will be appreciated that by using the sleeve 74, the excess tether can be left longer than without the use of a sleeve 74 allowing the tether to lie down, reducing the thickness of the bladder portion 52. It will also be appreciated that the sleeve 74 may have radiopaque material on an external surface thereof to either replace the radiopaque band 64 or be used in conjunction with the band. Alternatively, the radiopaque band 64 may be positioned over the sleeve 74 or knot. The sleeve 74 is provided on the kidney portion 54 and/or the bladder portion 52 to cover knots on the outside of the kidney and/or bladder portion. It will be appreciated, however, that a stent may be provided having knots on the inside of the bladder portion and/or the kidney portion, in which case the sleeve may be omitted.

When the stent 50 is positioned in the body of the patient, the one or more tethers 56 extend from the ureteral passageway 16, through the ureter orifice 20 and into the bladder 14. The one or more tethers 56 allow the bladder portion 52 to anchor the kidney portion 54 to keep the ureter portion 78 in position in the ureteral passageway 16, for example to prevent the ureter portion 78 from curling up. The tether also allows the ureter orifice 20 to freely move between the compressed state and the uncompressed state to allow the ureter orifice to move to the compressed state when the bladder fills, thereby preventing urine from moving backwards. The tether also allows urine to pass in its normal direction from the kidney to the bladder. In this way, the tether prevents or minimizes urinary reflux, flank pain, patient discomfort, etc.

The one or more tethers 56 additionally allow the bladder portion 52 to move freely in the bladder 14, for example as the bladder fills with urine, to prevent the bladder portion 54 from irritating the trigone; to prevent or minimize bladder spasms, blood in the urine and a constant urge to urinate; and to avoid a rigid positioning of the stent that would hold the stent in one position over the trigone. The bladder portion thereby freely floats and/or dangles within the bladder, i.e. not held in a rigid position, and is constrained only by the length of the tether. When being positioned, the kidney portion 54 and the bladder portion 52 are restrained, i.e. substantially straightened, to allow the portions to be navigated through the patient. It should be appreciated that for purposes of positioning, at least the ureter portion 78 of the kidney portion 54 has an inner diameter that is less than an inner diameter of the bladder portion 52. Once the kidney portion 54 is positioned and a guidewire withdrawn, the kidney portion moves to its unrestrained shape where the resilient fixing portion 76 is secured in the kidney 10 and the ureter portion 78 extends from the kidney 10 into the ureteral passageway 16 to keep the passageway open near the kidney. Similarly, once the bladder portion 52 is positioned and the guidewire withdrawn, the bladder portion 52 moves to its unrestrained shape where the bladder portion 52 anchors the ureter portion 78 while allowing the ureter orifice 20 to freely move between the compressed state and uncompressed state.

Turning now to FIGS. 3-10, exemplary embodiments of the ureteral stent is shown at 150, 250, 350, 450, 550, 650, 750 and 850. The ureteral stents 150, 250, 350, 450, 550, 650, 750 and 850 are substantially the same as the above-referenced ureteral stent 50, and consequently the same reference numerals but indexed by 100, 200, 300, 400, 500, 600, 700 and 800 respectively are used to denote structures corresponding to similar structures in the stents. In addition, the foregoing description of the stent 50 is equally applicable to the stent 150, 250, 350, 450, 550, 650, 750 and 850 except as noted below. Moreover, it will be appreciated upon reading and understanding the specification that aspects of the stents may be substituted for one another or used in conjunction with one another where applicable.

Figure 3:
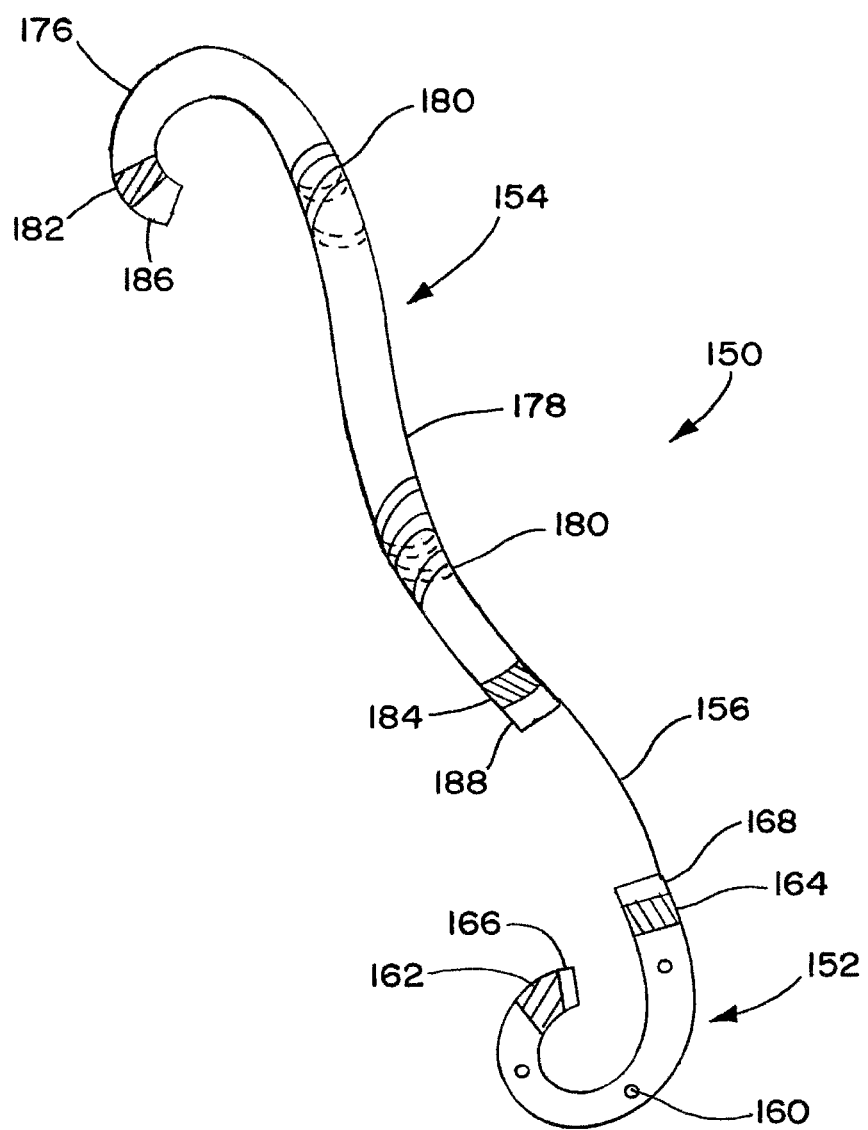
FIG. 3 is a schematic view of another exemplary stent.

Referring now to FIG. 3, the bladder portion 152 is a J-shaped flexible tube when unrestrained that prevents the bladder portion 152 from migrating into the ureteral passageway 16. Similarly, the fixing portion 176 of the kidney portion 154 is a J-shaped flexible tube when unrestrained to secure the kidney portion in the kidney 10. The second end 168 of the bladder portion 152 and the second end 188 of the kidney portion 154 are each coupled to a tether 156 in any suitable manner. The kidney portion 154 includes one or more spiral openings 180 extending through the wall of the kidney portion and the bladder portion 152 includes one or more circular openings 160 extending through the wall of the bladder portion to allow fluid to flow in/out of the kidney portion 154 and bladder portion 152. It will be appreciated that the bladder portion 152 may additionally or alternatively include one or more spiral openings extending through the wall of the bladder portion and the kidney portion 154 may additionally or alternatively include one or more circular openings extending through the wall of the kidney portion.

The kidney portion 154 has a diameter near the first end 186 that is larger than the diameter at the second end 188. For example, the diameter of the kidney portion may gradually taper down from the first end 186 to the second end 188. It will also be appreciated that the bladder portion 154 may have a diameter at the second end 168 that is larger than the diameter at the first end 166 of the bladder portion 152. Additionally, the diameter at the second end 168 of the bladder portion 152 may be substantially equal to or less than the diameter of the kidney portion at the second end 188, and the diameter at the first end 166 less than the diameter at the second end 168. Such a stent may be used as an endopyelotomy stent, providing a large diameter near the kidney for ureteral healing and a smaller diameter in the bladder for patient comfort.

Referring now to FIGS. 4 and 5, the bladder portions 252 and 352 are helical flexible tubes when unrestrained that prevent the bladder portions 252 and 352 from migrating into the ureteral passageway. Similarly, the fixing portions 276 and 376 of the kidney portions 254 and 354 are helical flexible tubes when unrestrained to secure the kidney portions in the kidney. The helical flexible tube portions 252, 352, 276, 376 of the bladder portions 252 and 352 and kidney portions 254 and 354 may have any suitable number of coils. The second ends 268 and 368 of the bladder portions 252 and 352 and the second ends 288 and 388 of the kidney portions 254 and 354 are each coupled to a respective tether 256, 356 in any suitable manner, such as by an adhesive that is covered by a sleeve.

The ureter portions 278 and 378 of the kidney portions 254 and 354 have varying lengths for use with patients having ureteral passageways of varying sizes, such as pediatric lengths and sizes, adult lengths and sizes, etc. As shown, the ureter portion 278 has a length L1 for use with a patient having a ureteral passageway of a first length, and the ureter portion 378 has a length L2, which is greater than the length L1, for use with a patient having a ureteral passageway of a second length greater than the first length. Additionally, the bladder portion 252 includes a substantially straightened portion 290 that is coupled to the tether, while the bladder portion 352 is formed without a straightened portion. It will be appreciated that the substantially straightened portion 290 may be included in the bladder portion 352 and not included in the bladder portion 252.

Figures 6, 6A:
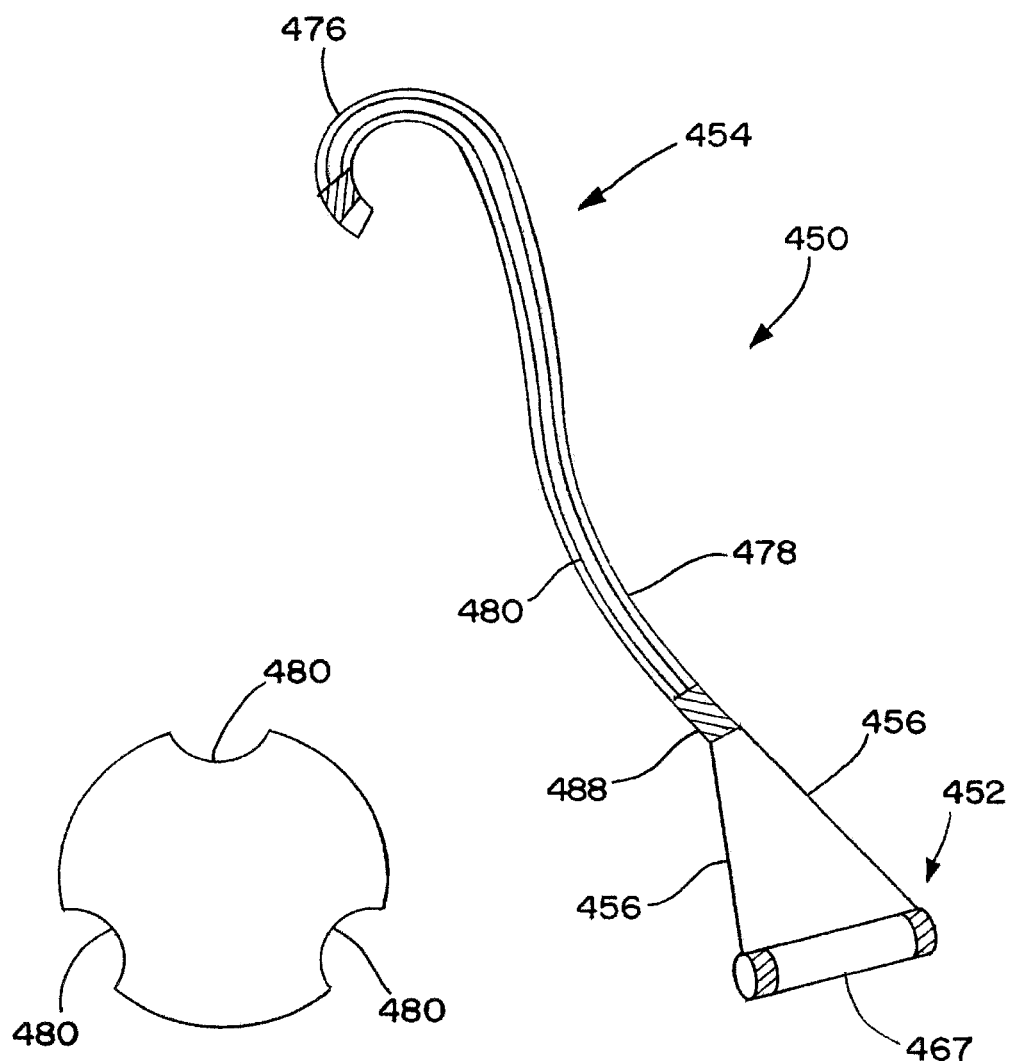
FIG. 6 is a schematic view of a further exemplary stent.
FIG. 6A is a top view of a kidney portion of the stent of FIG. 6.

Referring now to FIG. 6, the bladder portion 452 is a t-bar that prevents the bladder portion 452 from migrating into the ureteral passageway. The kidney portion 454 is shown as a J-shaped flexible tube, although it will be appreciated the kidney portion may have any suitable shape as discussed above. Ends of a tubular portion 467 of the t-bar and the second end 488 of the kidney portion 454 are coupled to two suitable tethers in any suitable manner, for example, by knots on the outside of the t-bar and/or ureter portion 478 that are covered by a sleeve as discussed above or by knots on an inside of the ends of the tubular portion 467 and/or ureter portion 478.

The bladder portion 452 and/or kidney portion 454 may include one or more channels 480 along the length thereof that are provided to guide fluid, such as urine, out of the kidney 10 and into the bladder 14. For example, FIG. 6A shows a top view of the kidney portion 454 including three channels 480 that are circumferentially spaced around the kidney portion 454. The channels 480 may be evenly circumferentially spaced around the kidney portion 454 or spaced in any other suitable manner.

Referring now to FIGS. 7 and 8, the stent 550 is formed by extruding the stent to form a flexible tubular member 600. Then at region 602, a section of the tubular member 600 is removed to form the tether 556. Before or after removing the section at region 602, geometric modifications, such as forming the fixing elements 552 and 554, adding retention notches, openings, etc. may be performed, for example by heat-forming, and surface edge softening may be performed.

Figure 9:
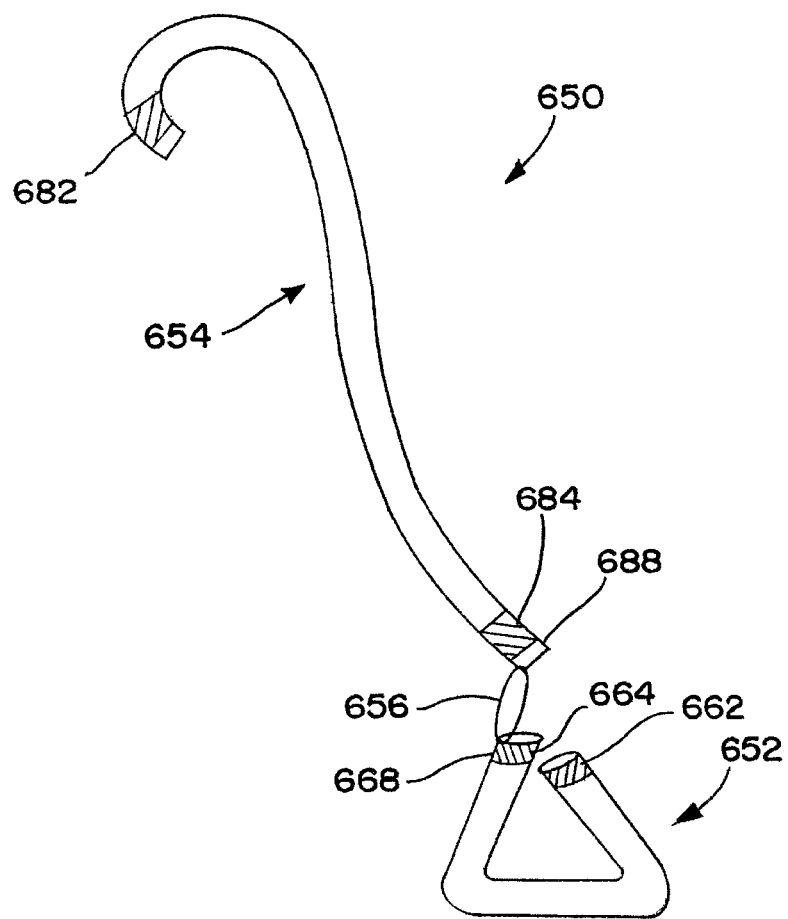
FIG. 9 is a schematic view of yet another exemplary stent.

Referring now to FIG. 9, the kidney portion 654 is a J-shaped flexible tube when unrestrained that secures the kidney portion 654 in the kidney 10. The bladder portion 652 is substantially triangular when unrestrained to prevent the bladder portion 652 from migrating into the ureteral passageway 16. The second end 668 of the bladder portion 652 and the second end 688 of the kidney portion 654 are each coupled to a tether 656 in any suitable manner. During positioning, the substantially triangular bladder portion is substantially straightened.

Figure 10:
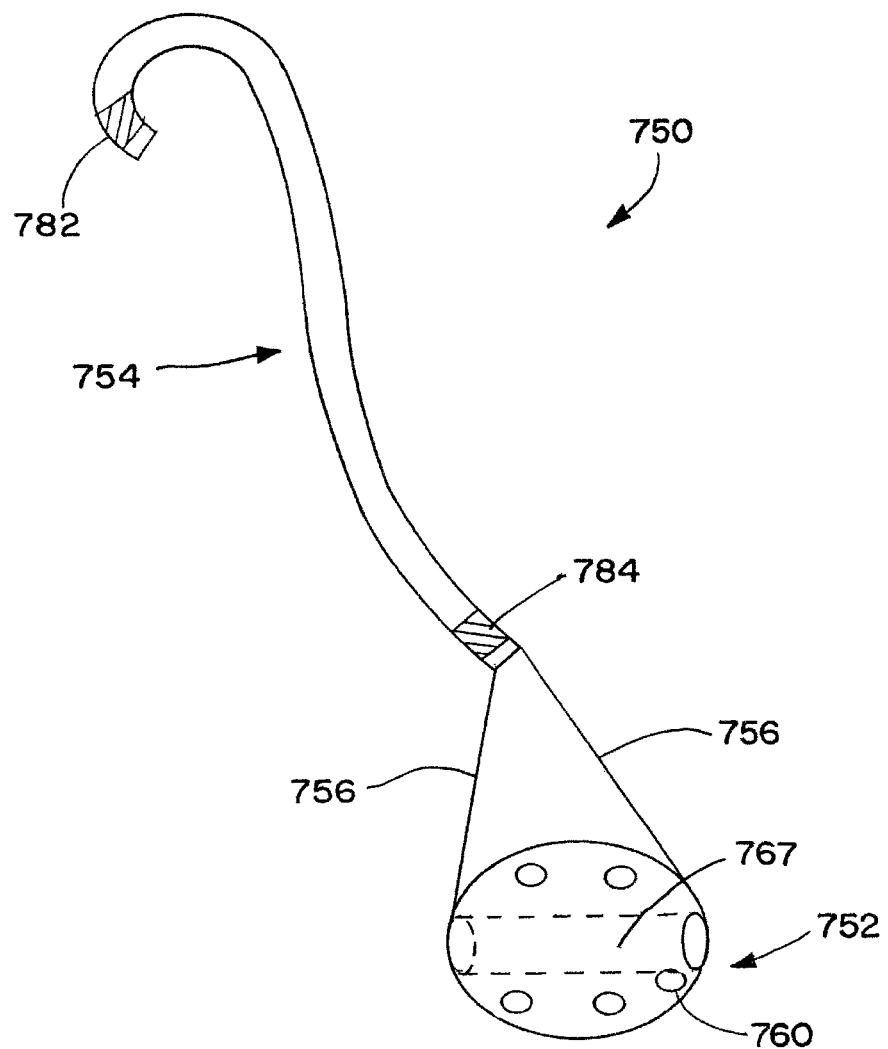
FIG. 10 is a schematic view of a further exemplary stent.

Referring now to FIG. 10, the kidney portion 754 is a J-shaped flexible tube when unrestrained that secures the kidney portion 754 in the kidney 10. The bladder portion 752 is substantially circular and sized to be larger than the ureter orifice 20 to prevent the bladder portion 752 from migrating into the ureteral passageway 16. The bladder portion 752 includes a through-hole 767 extending therethrough and one or more openings 760 extending through the bladder portion. The bladder portion may also include a seat at one end of the through-hole 767 for an end of a pusher to seat against during placement.

Figure 11:
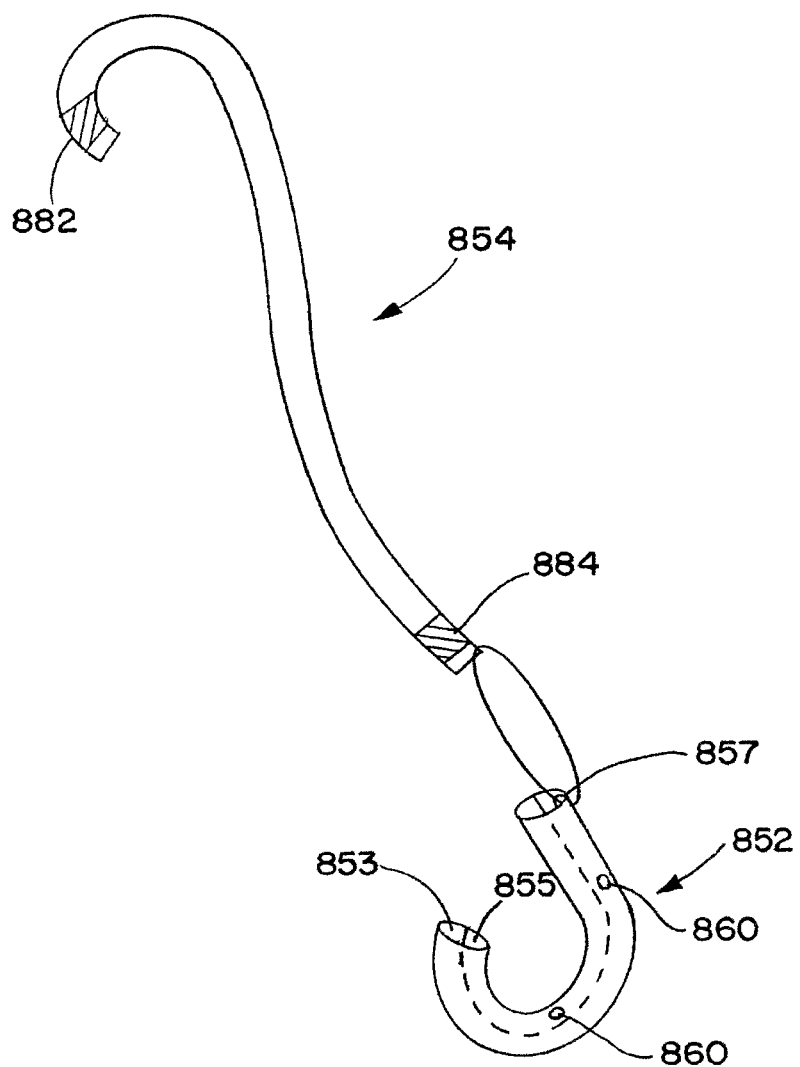
FIG. 11 is a schematic view of a yet further exemplary stent.

Referring now to FIG. 11, the kidney portion 854 is a J-shaped flexible tube when unrestrained that secures the kidney portion 854 in the kidney 10. Similarly, the bladder portion 852 is a J-shaped flexible tube when unrestrained that prevents the bladder portion 852 from migrating into the ureteral passageway 16. The bladder portion 852 includes a first lumen 853 for the knot 857 to be disposed to prevent the knot from irritating the trigone area, for example, and a second lumen 855 for receiving a stent pusher assembly and guidewire. One or more openings 860 may be provided in the first and/or second lumens that allow fluid to flow in/out of the bladder portion. Similarly, the kidney portion may include a first lumen for a knot to be disposed and a second lumen for receiving a guidewire.

Figure 12:
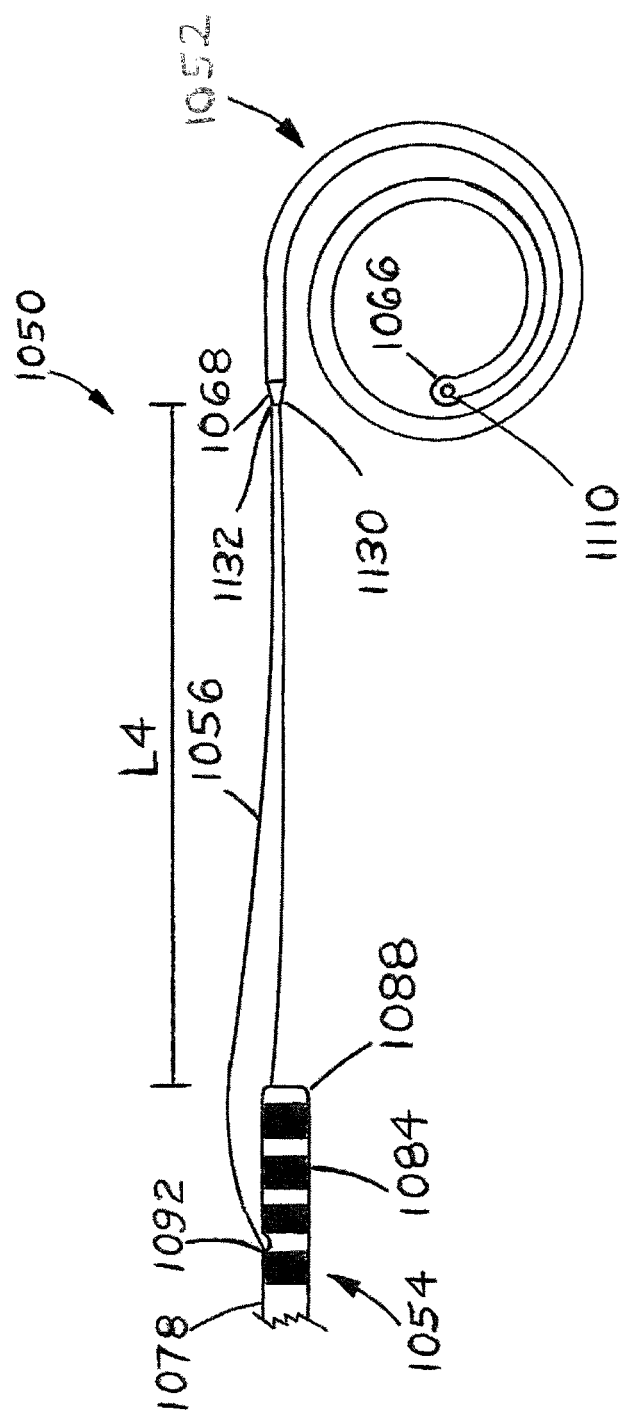
FIG. 12 is a partial side view of still another exemplary stent.
Figure 13:
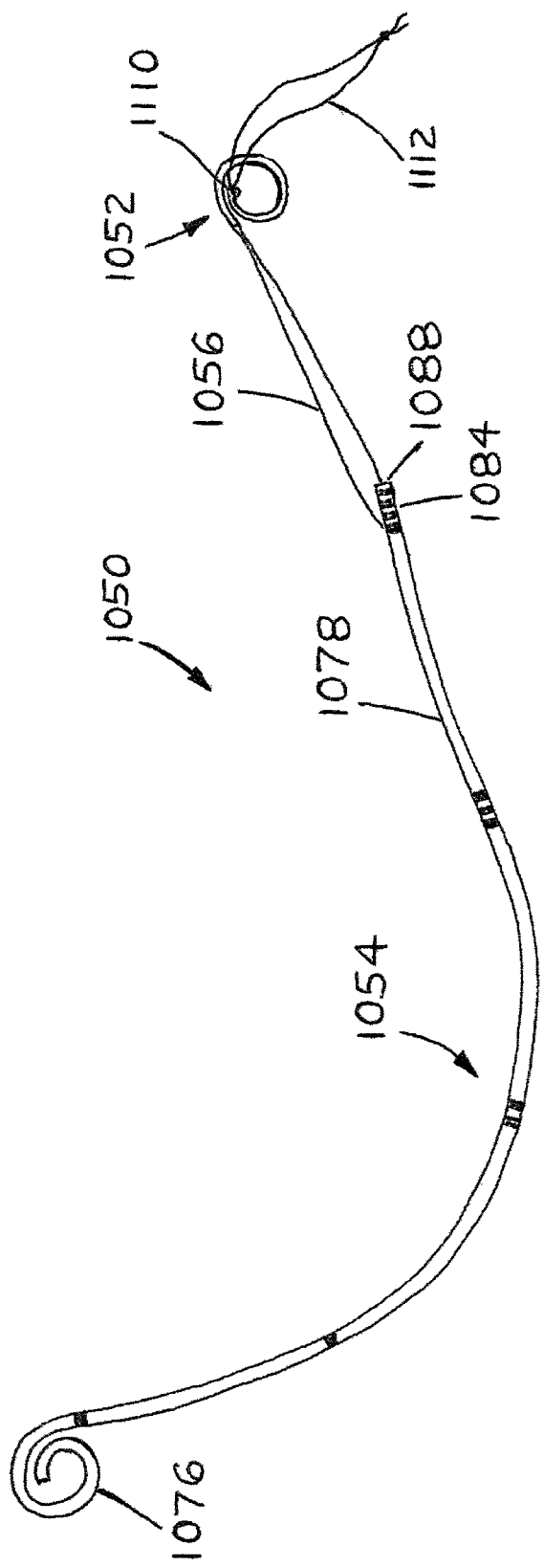
FIG. 13 is a side view of the stent of FIG. 12.

Turning now to FIGS. 12 and 13, an exemplary embodiment of the stent is shown at 1050. The stent 1050 is substantially the same as the above-referenced stent 50, and consequently the same reference numerals but indexed by 1000 are used to denote structures corresponding to similar structures in the stents. In addition, the foregoing description of the stent 50 is equally applicable to the stent 1050 except as noted below.

The ureteral stent 1050 includes a solid bladder portion 1052 positionable in the bladder, a kidney portion 1054 positionable in the kidney and the ureteral passageway, and a tether 1056 connecting the bladder portion and the ureter portion. The tether may include markings, such as barium markings along its length or integrally woven into the tether to assist in placing the ureteral stent 1050.

The solid bladder portion 1052 could be used with kidney portion 1054 or any of the above described kidney portions. The solid bladder portion 1052, or monofilament bladder portion, does not have a lumen allowing the bladder portion 1052 to have a smaller diameter than bladder portions of traditional stents while maintaining the same or substantially the same uncoil force of the traditional bladder portions. The smaller diameter allows the bladder portion to be inserted into a rigid cystoscope alongside a pusher tube thereby avoiding loading the bladder portion onto a guidewire.

In an embodiment, the bladder portion has a diameter between 0.025 and 0.050 inches. In an embodiment, the bladder portion has a diameter between 0.025 and 0.035. In an embodiment the bladder portion has a diameter less than or equal to about 0.035 inches. For example, a bladder portion having a diameter of about 0.035 inches could be inserted into a lumen of the cystoscope alongside a 7 French stent pusher. The bladder portion may be made of any suitable material in any suitable way, such as by injection molding the bladder portion out of a polymer, such as polypropylene, heat forming, extrusion, etc. In an embodiment, the polymer can be molded with a radiopaque filler, such as barium or bismuth, allowing for precise control of the radiopaque filler in the polymer.

For example, the bladder portion may be made by taking a straight piece of monofilament polymer extrusion and wrapping and restraining the extrusion around a helical threaded rod. The extrusion, now in the form of a coil, and the threaded rod are then heated, such as by a heat gun, to a predetermined temperature, such as a temperature below a sub-melt temperature of the polymer. The coil and rod are then dipped in cold water to set the polymer molecules in the coil shape. A coil section can then be cut off of the larger coil to provide a 450 degree circular coil section. One end of the coil is flattened to form an eyelet flange and a hole is punched through the flattened flange to complete the formation of the eyelet distal end. Edges of the eyelet may then be sanded down. The opposite end of the coil is then inserted into a hypodermic tube having an inside diameter large enough to form a snug slip fit over the coil monofilament diameter and having a suitable length, such as 0.125 inches. The ends of the tether, which have been looped through the opening in the kidney portion, are inserted into the other end of the hypodermic tubing and advanced until they touch the coil. The hypodermic tube is then heated via a suitable heat source until the coil and tether ends melt, and the ends of the tether can be advanced further towards the coil forming a flow melt union. The tube can then be removed from the heat source and then removed from the tether, such as by a grinding technique to remove the tube wall allowing the tether to be removed. Alternatively, the tube could be replaced by impulse heated pliers with a lumen or an open and close impulse heated mold with a lumen.

The solid bladder portion 1052 has first and second ends 1066 and 1068. An eyelet 1110 is formed at the first end 1066 for receiving a tether 1112, such as a pullout suture for removing the ureteral stent 1050 from the patient. The eyelet may be integrally formed with the rest of the bladder portion, for example during molding, or may be attached to the first end 1066 of the bladder portion 1052 in any suitable manner, such as by flattening the monofilament and punching a hole through the end, melt flowing a loop with the bladder portion, insert molding a loop onto a head formed bladder portion, etc.

The second end 1068 is conical allowing first and second ends 1130 and 1132 of the tether 1056 to be coupled to the second end 1068, for example by a flow melt process, and have a smooth transition between the tether 1056 and the bladder portion 1052 to prevent irritation of the bladder. By attaching the tether 1056 to conical second end 1068, by reducing the diameter of the bladder portion 1052, and by being free of a lumen, the bladder portion 1052 can be delivered without a guidewire 1114 running through a lumen, which could create friction or tangle with the tether in a lumen. Alternatively, the bladder portion 1052 could be formed with eyelets at the first and second ends and the tether 1056 could be secured to the eyelet at the second end, such as by knotting.

In another embodiment, the bladder portion could be formed by a suture having a larger diameter than the tether 1056, such as a diameter of 0.021 inches. The ends of the suture could be knotted, and the tether could be coupled to one knot, such as by tying or melting the sutures together, and the pull-out suture could be coupled to the other knot, such as by tying or melting the sutures together.

Referring now to the kidney portion 1054, the kidney portion may be tubular and is formed by a resilient fixing portion 1076 and a ureter portion 1078 extending from the resilient fixing portion. The kidney portion 1054 may include one or more radiopaque bands spaced along its length, such as bands 1084 near a second end 1088 of the kidney portion 1054. The kidney portion 1054 also includes an opening 1092 near the second end 1088 for receiving the tether 1056. One of the first or second ends 1130 and 1132 is inserted through the opening 1092 into a lumen of the kidney portion 1054 such that a portion of the tether is disposed inside the lumen and extends out an opening of the lumen at the second end 1088 and a portion of the tether 1056 extends outside the kidney portion 1054. The ends are then secured to the bladder portion 1052 as discussed above.

Figure 14:
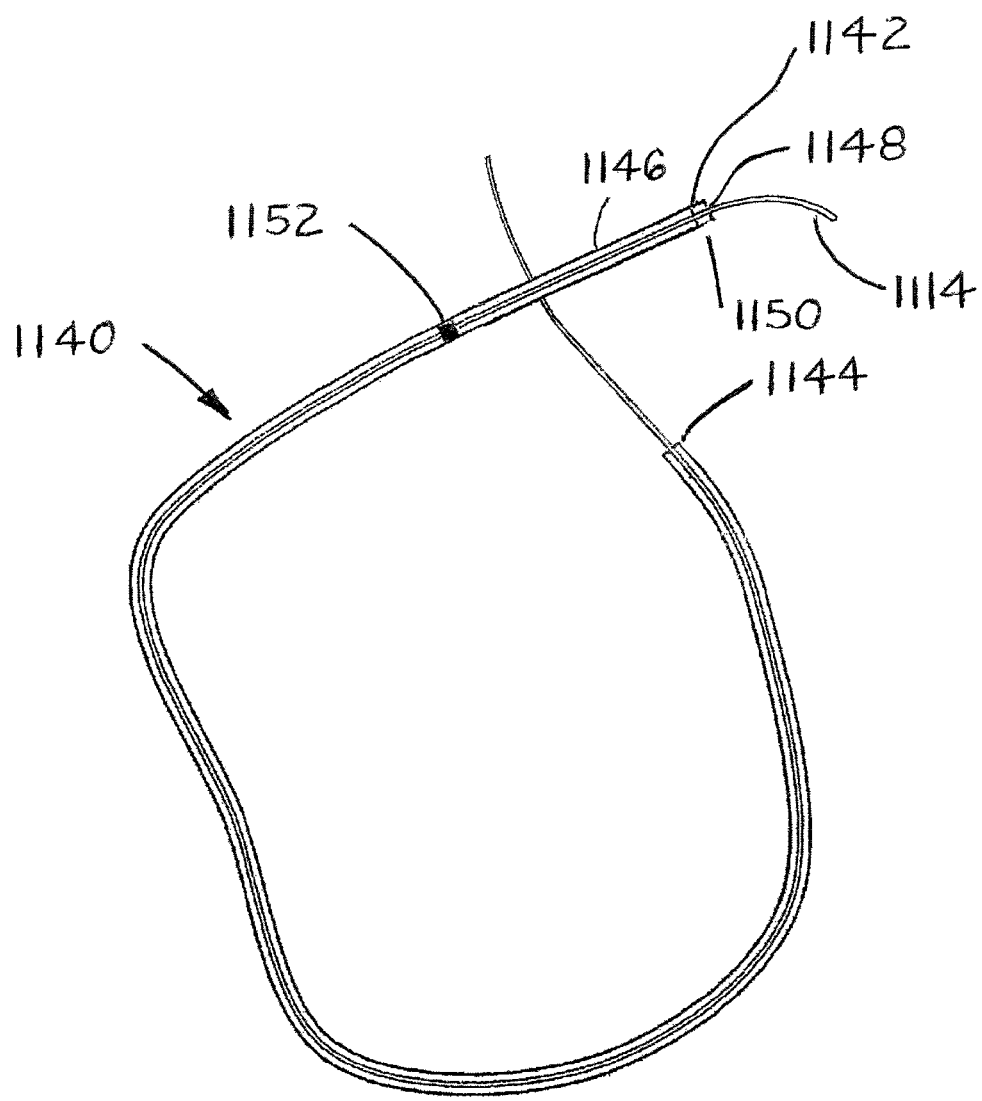
FIG. 14 is a fragmentary cross-sectional view of an exemplary stent pusher and a guidewire.
Figure 15:
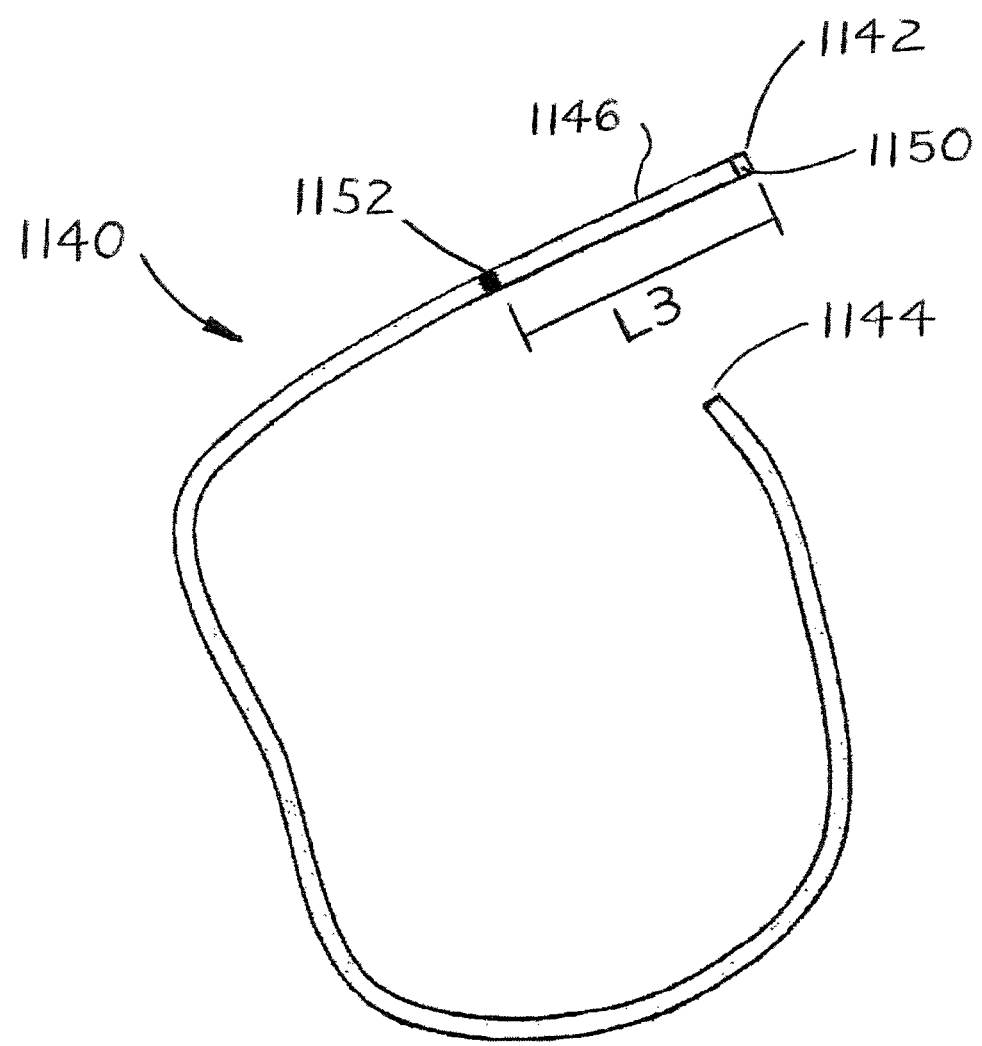
FIG. 15 is a side view of the stent pusher of FIG. 14.

Turning now to FIGS. 14 and 15, a stent pusher for delivering the ureteral stent 1050 into the kidney, ureteral passageway, and bladder is shown at reference numeral 1140. The stent pusher 1140 has a first end 1142 configured to abut the second end 1088 of the kidney portion 1054 and a second end 1144 opposite the first end that is manipulated by a surgeon during placement. The stent pusher 1140 has a body 1146 that may be any suitable shape, such as a tubular member, and a lumen 1148 extending through the body 1146. The stent pusher includes a tip 1150 secured to the body 1146 at the first end 1142. The tip 1150, which may be a stainless steel radiopaque tip, has a stiffness greater than the stiffness of the body 1146. The tip 1150 may be secured to the body 1146 in any suitable manner or may be molded with the body 1146.

The stent pusher 1140 also includes a band 1152 proximate the first end 1142. The band may be a marker if using direct visualization or a radiopaque band if using fluoroscopy or direct visualization. The band is used to provide an indication to the surgeon of how far the stent pusher 1140 should be advanced through the ureteral passageway. An end of the band closest to the first end 1142 of the stent pusher 1140 is a distance L3 from the end 1142, which coincides with a distance L4 (FIG. 12), which is the distance of the tether 1056 from the second end 1068 of the bladder portion 1052 to the second end 1088 of the kidney portion 1054.

The stent pusher 1140 has a diameter that is larger than the diameter of the kidney portion 1054 to prevent the stent pusher 1140 from entering the lumen of the kidney portion 1054. For example, the stent pusher 1140 may have a diameter of 7 French and the kidney portion has a diameter of 6 French. The bladder portion 1052 has a diameter less than the diameter of kidney portion 1054, as noted above, such that the diameters of the bladder portion 1052 and the stent pusher 1140 combined are less than a diameter of a channel of the cystoscope.

Figure 16:
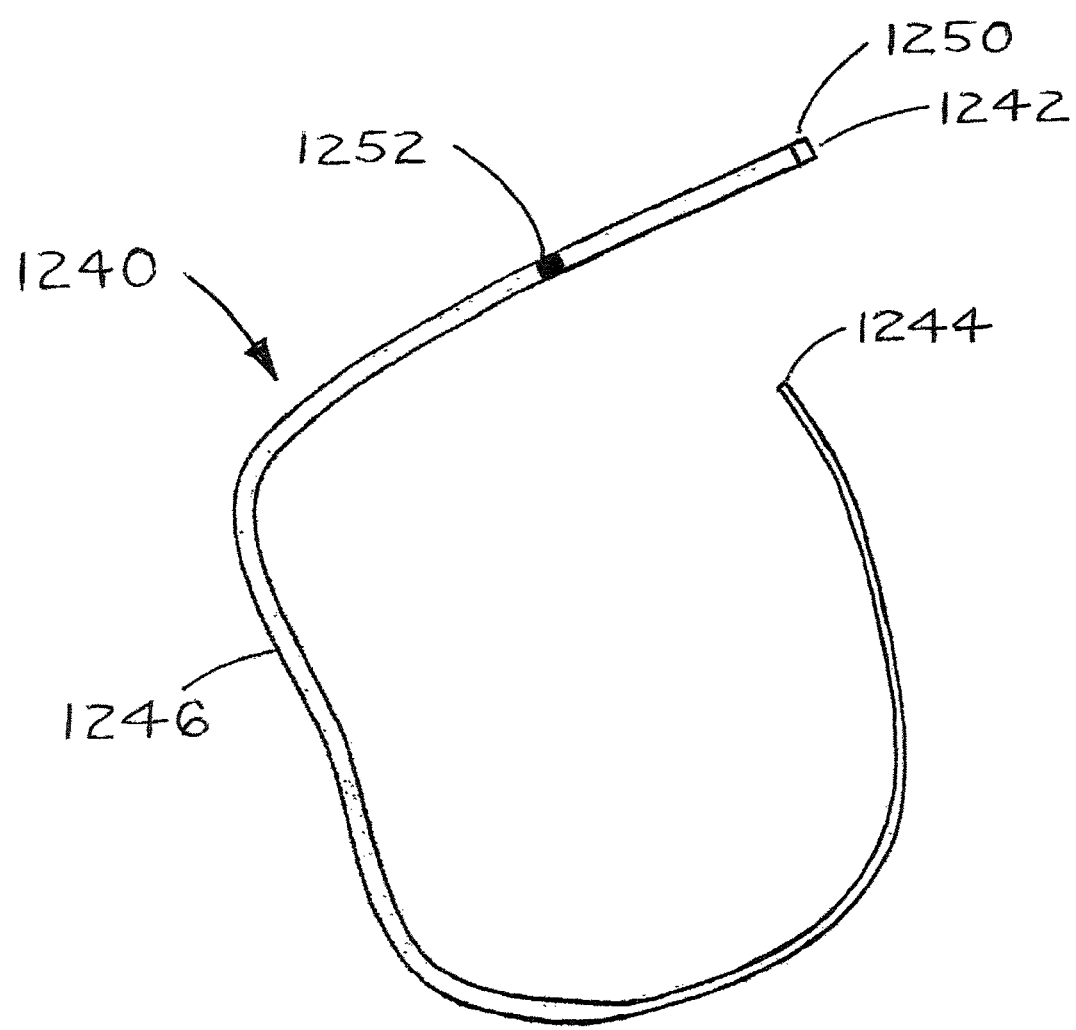
FIG. 16 is a side view of another exemplary stent pusher.

Turning now to FIG. 16, an exemplary embodiment of the stent pusher is shown at 1240. The stent pusher 1240 is substantially the same as the above-referenced stent pusher 1140, and consequently the same reference numerals but indexed by 100 are used to denote structures corresponding to similar structures in the pushers. In addition, the foregoing description of the stent pusher 1140 is equally applicable to the stent pusher 1240 except as noted below.

The stent pusher 1240 has a first end 1242 configured to abut the second end 1088 of the kidney portion 1054 and a second end 1244 opposite the first end that is manipulated by a surgeon during placement. The stent pusher 1240 has a body 1246 and a lumen (not shown) extending through the body 1246. The stent pusher includes a tip 1250 and a band 1252.

The first end 1242 of the stent pusher has a first diameter greater than a second diameter of the second end of the stent pusher so that the bladder portion can move through the channel of the cystoscope alongside the second diameter portion while the first diameter portion can be moved through the channel alongside the tether and be sized to have sufficient column strength to push the kidney portion without buckling. For example, the first diameter of the stent pusher 1240 could be 6 French and the second diameter of the stent pusher 1240 could be 4 French. The stent pusher could gradually reduce its diameter from the first diameter to the second diameter or reduce its diameter rapidly.

Figure 17:
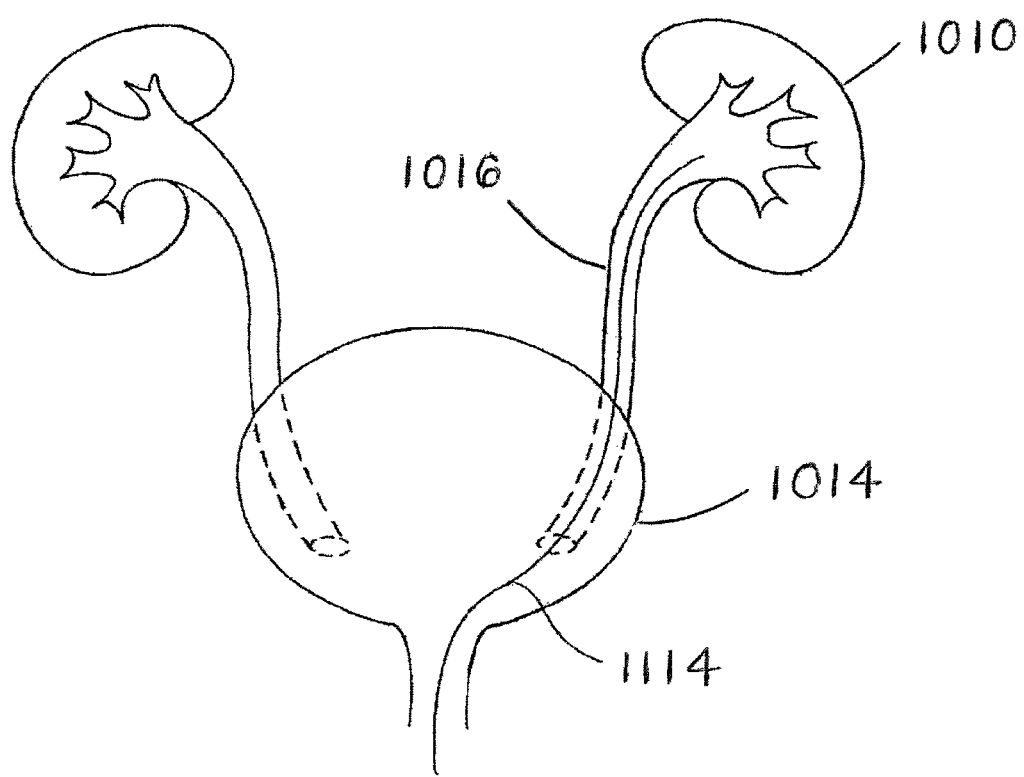
FIG. 17 is a schematic view of a guidewire being inserted into the patient.
Figure 18:
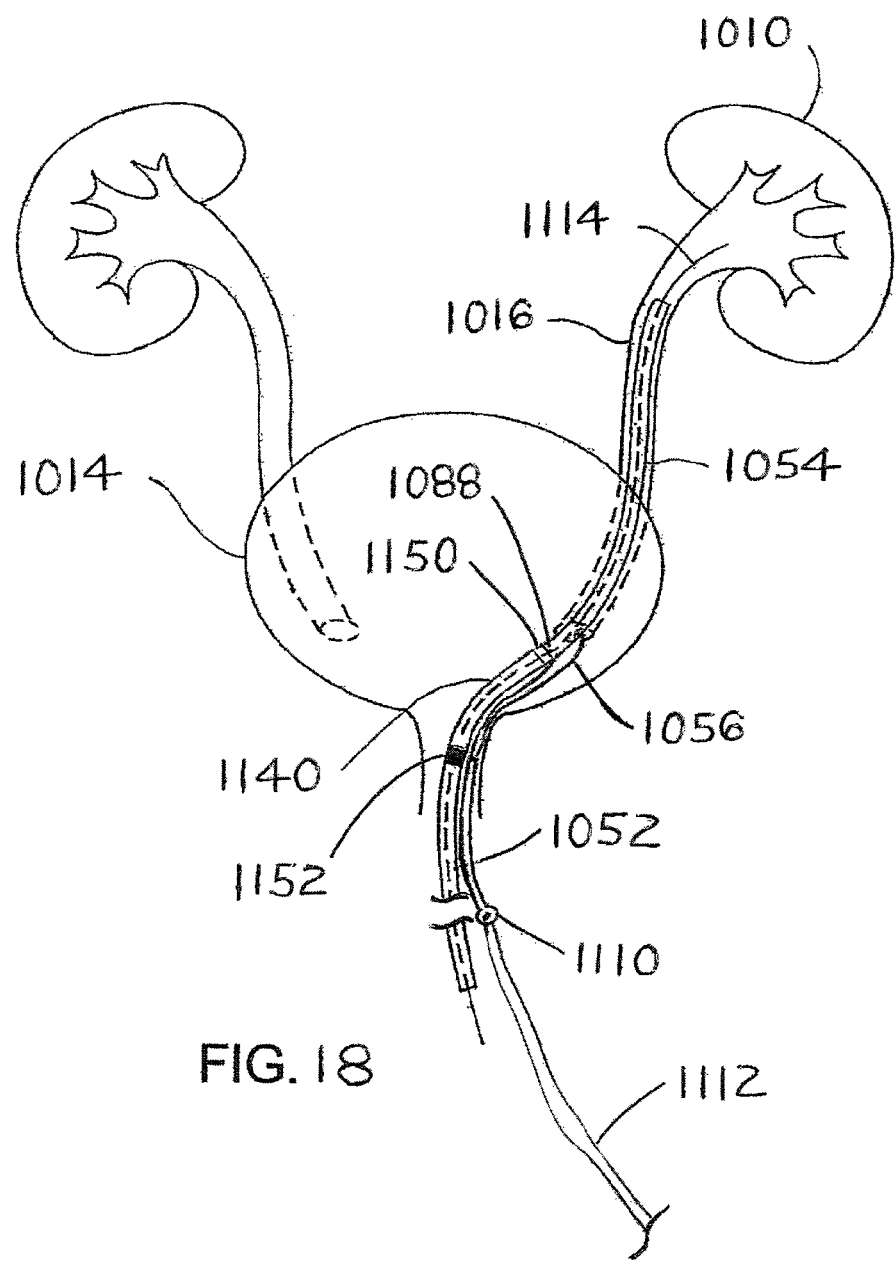
FIG. 18 is a schematic view of the stent of FIG. 12 being positioned in the patient by the stent pusher of FIG. 14.
Figure 19:
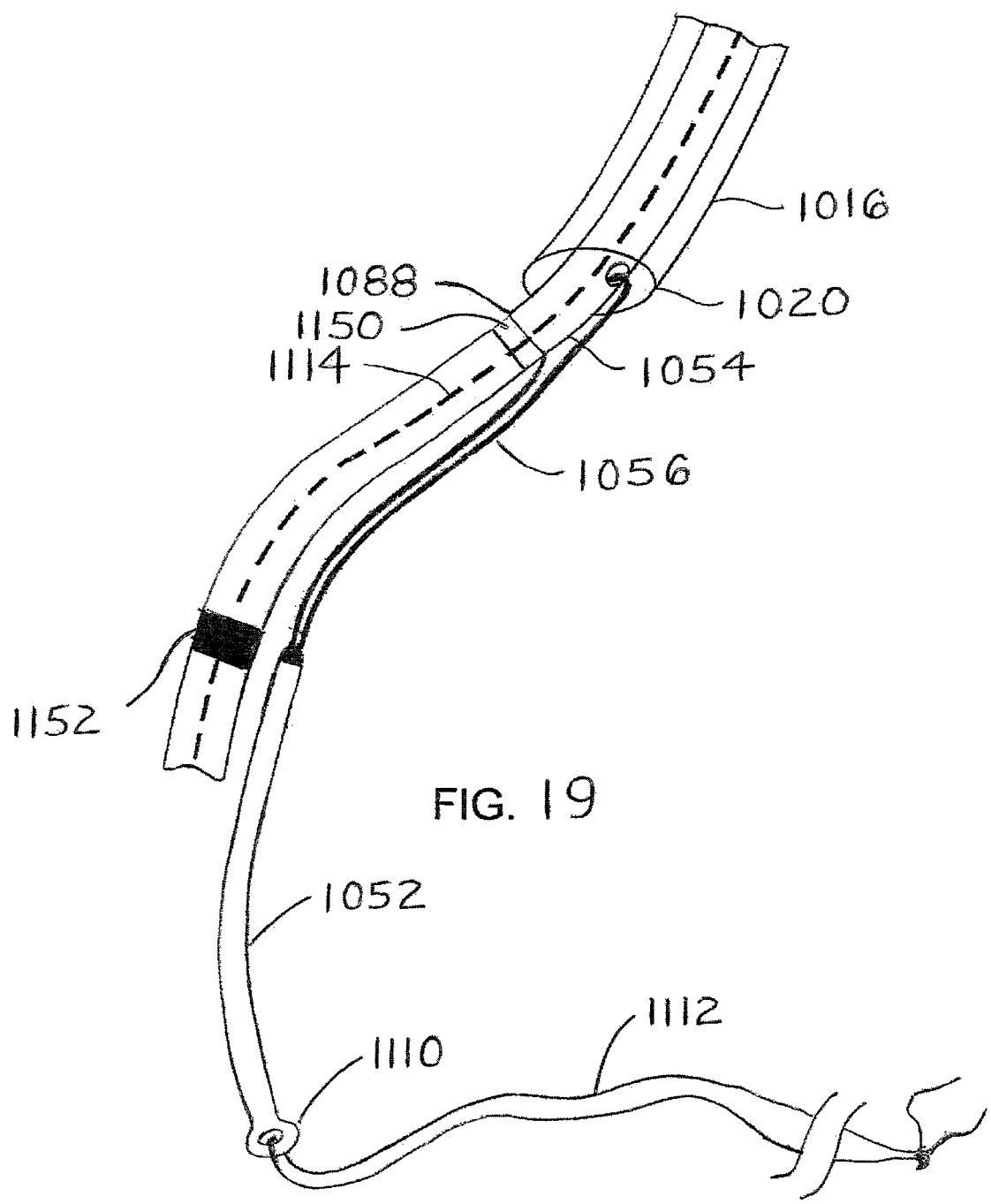
FIG. 19 is another schematic view of the stent of FIG. 12 being positioned in the patient by the stent pusher of FIG. 14.

Turning now to FIGS. 17-22 in addition to FIGS. 12-15, a method of placing the ureteral stent 1050 will be discussed. As shown in FIG. 17, the method begins with the guidewire 1114 being inserted through the bladder 1014, into the ureteral passageway 1016 and into the kidney 1010. The kidney portion 1054 is then advanced over the guidewire 1114 outside the patient. It will be appreciated, however, that the kidney portion 1054 can be advanced over the guidewire 1114 prior to the guidewire being positioned. As shown in FIGS. 18 and 19, the stent pusher 1140 is then advanced over and along the guidewire 1114 until the tip 1150 of the stent pusher abuts the second end 1088 of the kidney portion 1054. The stent pusher 1140 is then advanced into the patient, thereby advancing the stent 1050 into the patient. FIGS. 18 and 19 show the kidney portion 1054 substantially positioned in the ureteral passageway, with the second end 1088 of the kidney portion 1054 being positioned in the bladder 1014 near the ureter orifice 20.

Figure 20:
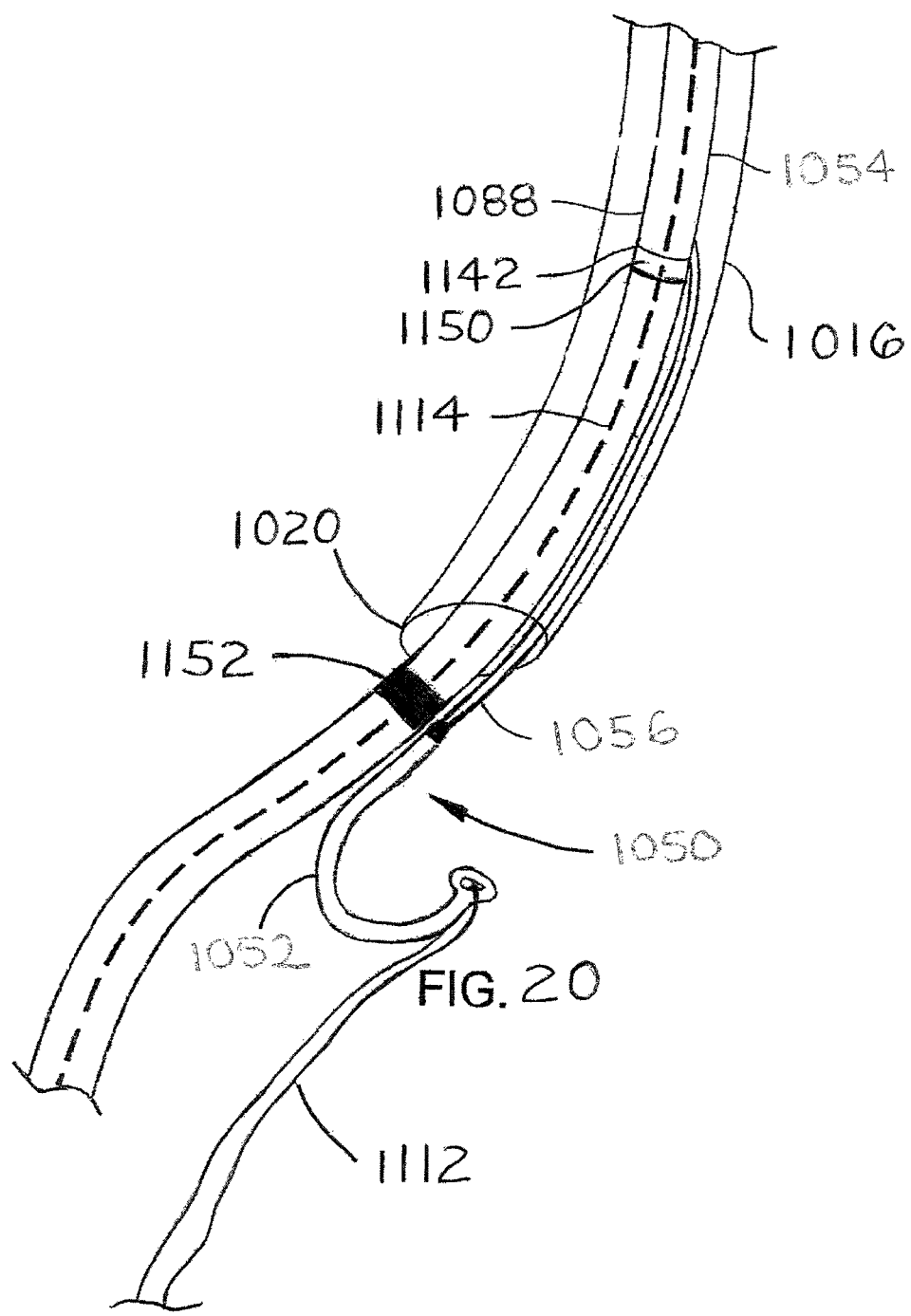
FIG. 20 is still another schematic view of the stent of FIG. 12 being positioned in the patient by the stent pusher of FIG. 14.
Figure 21:
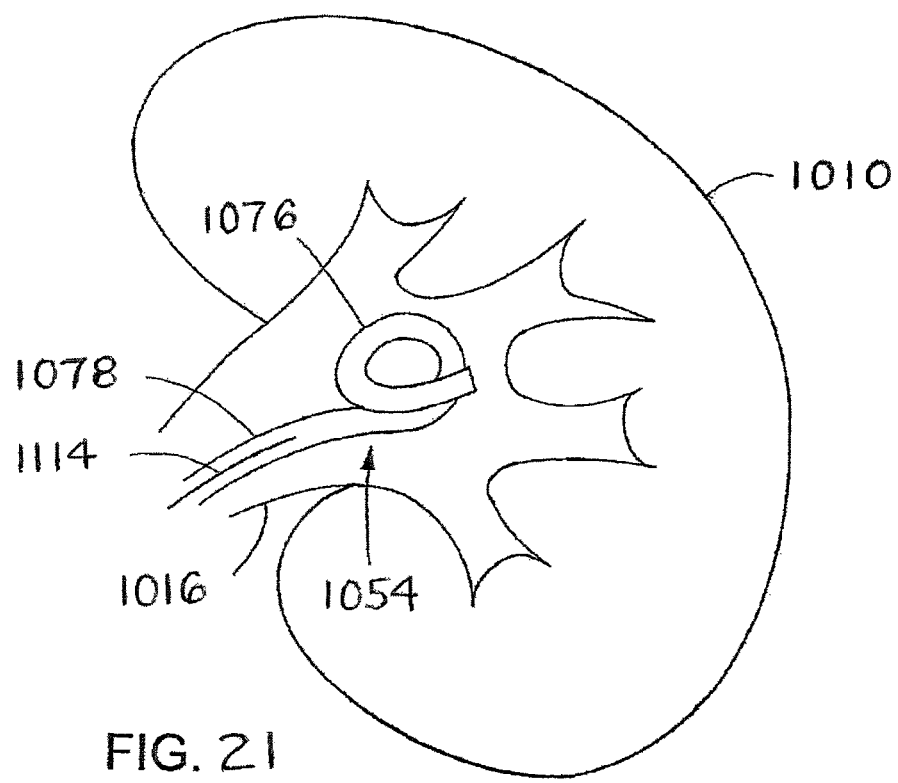
FIG. 21 is a schematic view of a kidney with a kidney portion of the stent inserted therein.
Figure 22:
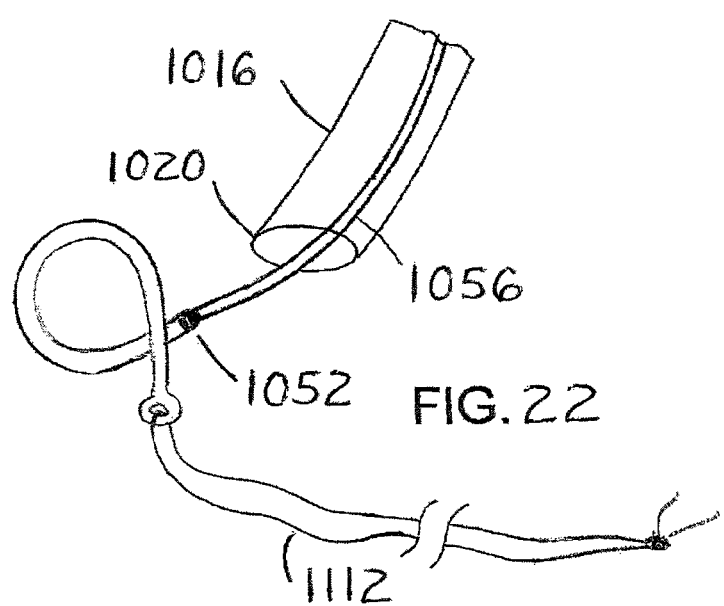
FIG. 22 is a schematic view of a ureteral passageway and bladder with a bladder portion of the stent inserted therein.

As shown in FIG. 20, the stent pusher 1140 is advanced further into the patient such that the tip 1150 of the stent pusher 1140 enters the ureteral passageway. The stent pusher 1140 is advanced until the band 1152 is aligned with or substantially aligned with the ureter orifice 1020, thereby indicating to the surgeon that the kidney portion 1054 is positioned in the kidney and ureteral passageway and that the bladder portion 1052 is positioned in the bladder. The stent pusher 1140 and guidewire 1114 can then be withdrawn from the patient, for example by removing or partially withdrawing the guidewire allowing the kidney portion 1154 to move to the unrestrained position shown in FIGS. 21 and then removing the stent pusher and guidewire either separately or simultaneously. When unrestrained, the fixing portion 1076 secures the kidney portion 1054 in the kidney 1010, and the ureter portion 1078 extends from the kidney 1010 into the ureteral passageway 1016 to keep the passageway open. As shown in FIG. 22, when positioned the bladder portion 1052 floats in the bladder and the pullout suture 1112 extends from the bladder outside the patient. Alternatively, the pullout suture 1112 can be removed prior to placement.

As discussed above, the stent and stent pusher may be guided fluoroscopically by the radiopaque elements on the stent and/or stent pusher, and/or by tracking markers on the stent and/or stent pusher. Additionally or alternatively, the stent may be positioned using a suitable endoscope.

Turning now to FIGS. 23-26, an exemplary embodiment of the stent is shown at 1350. The stent 1350 is substantially the same as the above-referenced stent 1050, and consequently the same reference numerals but indexed by 300 are used to denote structures corresponding to similar structures in the stents. In addition, the foregoing description of the stent 1050 is equally applicable to the stent 1350 except as noted below.

The ureteral stent 1350 includes a bladder portion 1352 positionable in the bladder, a kidney portion 1354 positionable in the kidney and the ureteral passageway, and a tether 1356 connecting the bladder portion and the ureter portion. The bladder portion 1352 has first and second ends 1366 and 1368 and an eyelet 1410 formed at the first end 1366 for receiving a tether. The kidney portion 1354 is formed by a resilient fixing portion and a ureter portion 1378 extending from the resilient fixing portion. The kidney portion 1354 may include one or more radiopaque bands 1384 spaced along its length, such as bands near a second end 1388 of the kidney portion 1354. The kidney portion 1354 also includes an opening 1392 near the second end 1388 for receiving the tether 1356.

The tether 1356 may be formed by molding, such as injection molding, and includes a first end 1430 and a second end 1432 having an eyelet 1460.

The first end 1430 of the tether 1356 is attached to the second end 1368 of the bladder portion 1352, for example by a flow melt process, and the second end 1432 of the tether 1356 is attached to the second end 1388 of the kidney portion 1354. In the illustrated embodiment, the second end 1432 is attached to the kidney portion 1354 by forming a loop around the second end 1388. For example, the second end 1432 of the tether is inserted through the opening 1392 into the lumen 1394 of the kidney portion 1354 and pulled out of the lumen 1394 at the second end 1388. The bladder portion 1352 is then moved through the eyelet 1460 by passing the eyelet 1410 through the eyelet 1460 and continuing to move the bladder portion 1352 through the eyelet 1460 and opening 1392 until the tether 1356 forms a loop 1462 around the kidney portion 1354 at the second end 1388. The loop is tightened and then a sleeve 1374, such as a heat shrink, tape, UV adhesive, etc. is coupled to the second end 1388 of the kidney portion to conceal the eyelet 1460 to prevent or minimize irritation to the patient.

Turning now to FIGS. 27-30, an exemplary embodiment of the stent is shown at 1550. The stent 1550 is substantially the same as the above-referenced stent 1050, and consequently the same reference numerals but indexed by 500 are used to denote structures corresponding to similar structures in the stents. In addition, the foregoing description of the stent 1050 is equally applicable to the stent 1550 except as noted below.

The ureteral stent 1550 includes a bladder portion 1552 positionable in the bladder, a kidney portion 1554 positionable in the kidney and the ureteral passageway, and a tether 1556 connecting the bladder portion and the ureter portion. The bladder portion 1552 has first and second ends 1566 and 1568 and an eyelet 1610 formed at the first end 1566 for receiving a tether. The kidney portion 1554 is formed by a resilient fixing portion and a ureter portion 1578 extending from the resilient fixing portion. The kidney portion 1554 may include one or more radiopaque bands 1584 spaced along its length, such as bands near a second end 1588 of the kidney portion 1554. The kidney portion 1554 also includes an opening 1592 near the second end 1588 for receiving the tether 1556.

The tether 1556 may be formed by molding, such as injection molding, and includes a first end 1630 and a second end 1632 having a rivet lock 1660 with a pin 1662. The first end 1630 of the tether 1556 is attached to the second end 1568 of the bladder portion 1552, for example by a flow melt process, and the second end 1632 of the tether 1556 is attached to the second end 1588 of the kidney portion 1554. In the illustrated embodiment, the second end 1632 is attached to the kidney portion 1554 by inserting the pin 1662 into the opening 1592 until the rivet lock 1660 abuts the outer surface of the ureter portion 1578. The rivet lock 1660 is then covered with a sleeve 1574, such as a heat shrink, tape, UV adhesive, etc. coupled to the second end 1588 of the kidney portion to capture and hold the rivet lock 1660 in place and to conceal the rivet lock 1660 to prevent or minimize irritation to the patient.

Turning now to FIGS. 31-34, an exemplary embodiment of the stent is shown at 1750. The stent 1750 is substantially the same as the above-referenced stent 1050, and consequently the same reference numerals but indexed by 700 are used to denote structures corresponding to similar structures in the stents. In addition, the foregoing description of the stent 1050 is equally applicable to the stent 1750 except as noted below.

The ureteral stent 1750 includes a bladder portion 1752 positionable in the bladder, a kidney portion 1754 positionable in the kidney and the ureteral passageway, and a tether 1756 connecting the bladder portion and the ureter portion. The bladder portion 1752 has first and second ends 1766 and 1768 and an eyelet 1810 formed at the first end 1766 for receiving a tether. The kidney portion 1754 is formed by a resilient fixing portion and a ureter portion 1778 extending from the resilient fixing portion. The kidney portion 1754 may include one or more radiopaque bands 1784 spaced along its length, such as bands near a second end 1788 of the kidney portion 1754. The kidney portion 1754 also includes an opening 1792 near the second end 1788 for receiving the tether 1756.

The tether 1756 may be formed by molding, such as injection molding, and includes a first end 1830 and a second end 1832. The first end 1830 of the tether 1756 is attached to the second end 1768 of the bladder portion 1752, for example by a flow melt process, and the second end 1832 of the tether 1756 is attached to the second end 1788 of the kidney portion 1754. In the illustrated embodiment, the second end 1832 is attached to the kidney portion 1754 by advancing the tether 1756 through the lumen 1794 of the kidney portion 1754 and out of the opening 1792 and then knotting the second end 1832 of the tether 1756 to form a knotted portion 1860 that is larger than a diameter of the opening 1792. The knotted portion 1860 is then covered with a sleeve 1774, such as a heat shrink, tape, UV adhesive, etc. coupled to the second end 1788 of the kidney portion to conceal the knotted portion 1860 to prevent or minimize irritation to the patient. Alternatively, the tether 1756 could be inserted through the opening 1792 into the lumen 1794 and then knotted, and then the tether 1756 covered with the sleeve 1774.

Turning now to FIGS. 35-38, an exemplary embodiment of the stent is shown at 1950. The stent 1950 is substantially the same as the above-referenced stent 1050, and consequently the same reference numerals but indexed by 900 are used to denote structures corresponding to similar structures in the stents. In addition, the foregoing description of the stent 1050 is equally applicable to the stent 1950 except as noted below.

The ureteral stent 1950 includes a bladder portion 1952 positionable in the bladder, a kidney portion 1954 positionable in the kidney and the ureteral passageway, and a tether 1956 connecting the bladder portion and the ureter portion. The bladder portion 1952 has first and second ends 1966 and 1968 and an eyelet 2010 formed at the first end 1966 for receiving a tether. The kidney portion 1954 is formed by a resilient fixing portion and a ureter portion 1978 extending from the resilient fixing portion. The kidney portion 1954 may include one or more radiopaque bands 1984 spaced along its length, such as bands near a second end 1988 of the kidney portion 1954. The kidney portion 1954 also includes openings 1992 and 1993 near the second end 1988 for receiving the tether 1956.

The tether 1956 may be formed by molding, such as injection molding, and includes a first end 2030 and a second end 2032. The first end 2030 of the tether 1956 is attached to the second end 1968 of the bladder portion 1952, for example by a flow melt process, and the second end 2032 of the tether 1956 is attached to the second end 1988 of the kidney portion 1954. In the illustrated embodiment, the second end 2032 is attached to the kidney portion 1954 by advancing the tether 1956 through the lumen 1994 of the kidney portion 1954 and out of the opening 1992, and then through the opening 1993 adjacent the opening 1992 into the lumen 1994 and out of the lumen 1994 at the second end 1988. The second end 2032 is then attached to another portion of the tether 1956 in a suitable manner, such as by spot welding, thereby forming a triangular shaped portion. The openings 1992 and 1993 and the tether 1956 passing through them are then covered with a sleeve 1974, such as a heat shrink, tape, UV adhesive, etc. coupled to the second end 1988 of the kidney portion to conceal the openings 1992 and 1993 and portion of the tether 1956 to prevent or minimize irritation to the patient.

Figure 39:
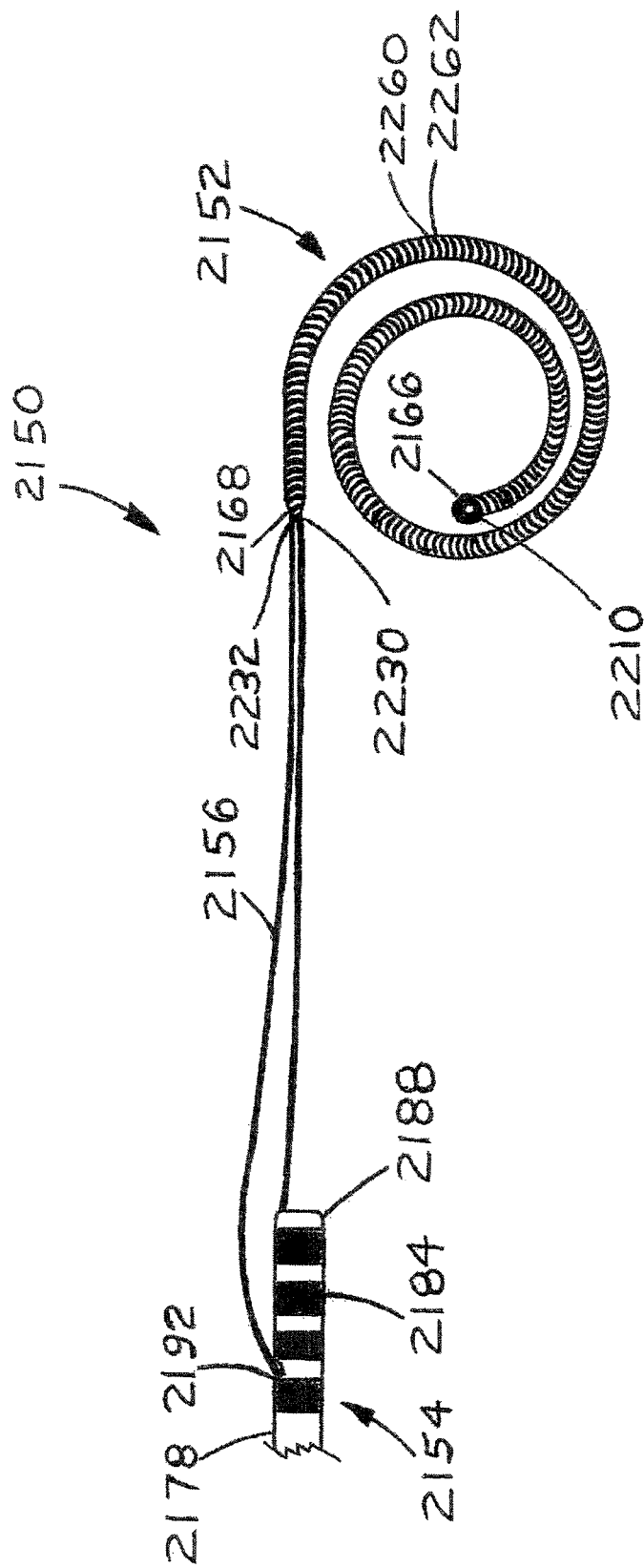
FIG. 39 is a partial side view of another exemplary stent.

Turning now to FIG. 39, an exemplary embodiment of the stent is shown at 2150. The stent 2150 is substantially the same as the above-referenced stent 1050, and consequently the same reference numerals but indexed by 1100 are used to denote structures corresponding to similar structures in the stents. In addition, the foregoing description of the stent 1050 is equally applicable to the stent 2150 except as noted below.

The ureteral stent 2150 includes a bladder portion 2152 positionable in the bladder, a kidney portion 2154 positionable in the kidney and the ureteral passageway, and a tether 2156 connecting the bladder portion and the ureter portion. The bladder portion 2152 has first and second ends 2166 and 2168 and an eyelet 2210 formed at the first end 2166 for receiving a tether. The bladder portion 2152 may be formed by two tethers 2260 and that are welded/fused at the second end 2168 and then twisted together to form a twisted composite filament. The eyelet 2210 is then formed by not twisting the tethers 2260 and 2262 at their ends at the first end 2166 and welding the tethers at the first end 2166. The bladder portion 2152 can then be wrapped around a helical rod, heated to a sub melt temperature, and then cooled to set the material to form the bladder portion 2152 in the desired shape.

The kidney portion 2154 is formed by a resilient fixing portion and a ureter portion 2178 extending from the resilient fixing portion. The kidney portion 2154 may include one or more radiopaque bands 2184 spaced along its length, such as bands near a second end 2188 of the kidney portion 2154. The kidney portion 2154 also includes an opening 2192 near the second end 2188 for receiving the tether 2156. One of the first or second ends 2230 and 2232 of the tether 2156 is inserted through the opening 2192 into a lumen of the kidney portion 2154 such that a portion of the tether is disposed inside the lumen and extends out an opening of the lumen at the second end 2188 and a portion of the tether 2156 extends outside the kidney portion 2154. The ends 2230 and 2232 are then secured to the bladder portion 1052 at the second end 2168, for example by a flow melt process. In an embodiment, a sleeve such as a heat shrink, tape, UV adhesive, etc. may be coupled to the second end 2188 of the kidney portion to conceal the opening 2192 and portion of the tether 2156 to prevent or minimize irritation to the patient.

Figure 40:
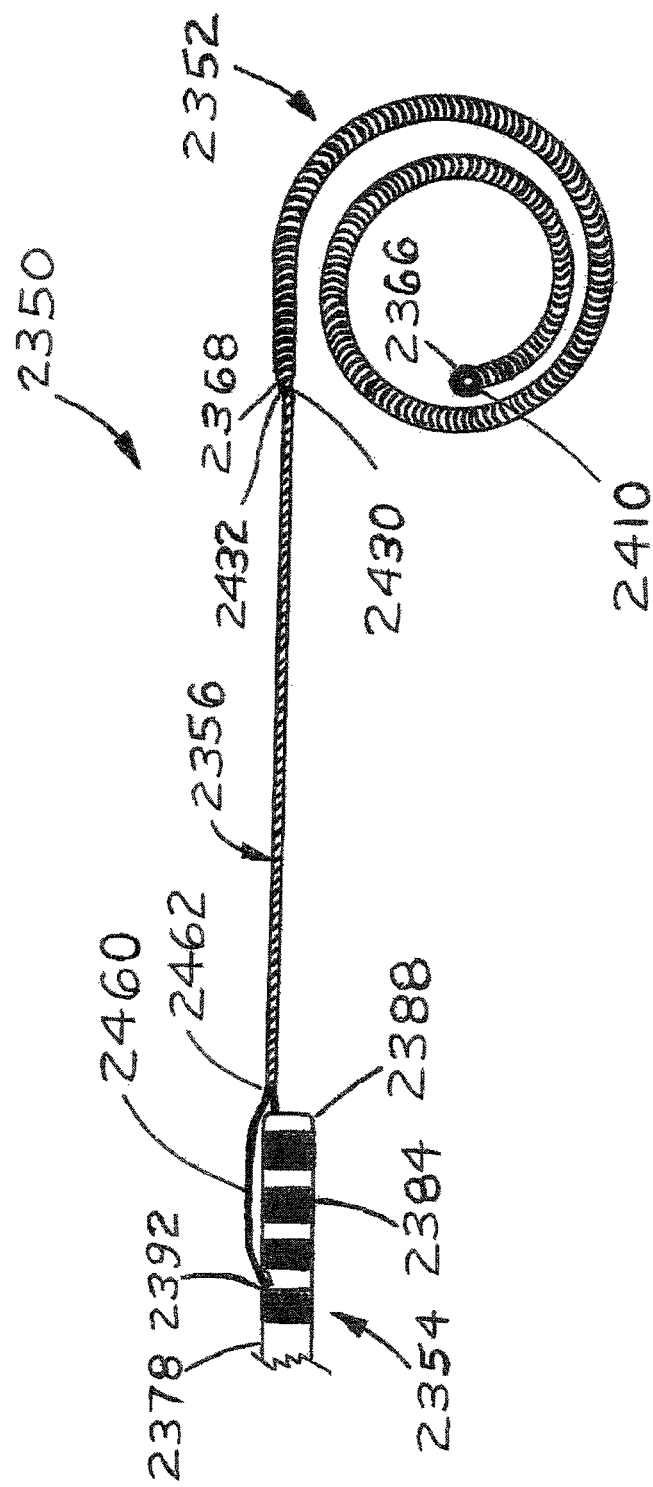
FIG. 40 is a partial side view of still another exemplary stent.

Turning now to FIG. 40, an exemplary embodiment of the stent is shown at 2350. The stent 2350 is substantially the same as the above-referenced stent 1050, and consequently the same reference numerals but indexed by 1300 are used to denote structures corresponding to similar structures in the stents. In addition, the foregoing description of the stent 1050 is equally applicable to the stent 2350 except as noted below.

The ureteral stent 2350 includes a bladder portion 2352 positionable in the bladder, a kidney portion 2354 positionable in the kidney and the ureteral passageway, and a tether portion 2356 connecting the bladder portion and the ureter portion. The kidney portion 2354 is formed by a resilient fixing portion and a ureter portion 2378 extending from the resilient fixing portion. The kidney portion 2354 may include one or more radiopaque bands 2384 spaced along its length, such as bands near a second end 2388 of the kidney portion 2354. The kidney portion 2354 also includes an opening 2392 near the second end 2388 for receiving a tether 2460 having first and second ends. One of the first or second ends of the tether 2460 is inserted through the opening 2392 into a lumen of the kidney portion 2354 such that a portion of the tether is disposed inside the lumen and extends out an opening of the lumen at the second end 2388 and a portion of the tether 2356 extends outside the kidney portion 2354.

The tether portion 2356 is then formed by welding/fusing the tether 2460 at point 2462 near the end 2388 of the kidney portion 2354 and twisting the portions of the tether 2460 together to form a twisted composite filament. The bladder portion 2352 is formed by continuing the twisting of the tether 2460 at the second end 2368 of the bladder portion to form a twisted composite filament, and an eyelet 2410 is formed at the first end 2366 of the bladder portion 2352 by not twisting the tether 2460 at its ends at the first end 2366 and welding the tether 2460 at the first end 2366. The bladder portion 2352 can then be wrapped around a helical rod, heated to a sub melt temperature, and then cooled to set the material to form the bladder portion 2352 in the desired shape. In the illustrated embodiment, the tether portion 2356 has a smaller diameter than the bladder portion 2352. This can be achieved in any suitable manner, such as by using a tether 2460 that is thicker at its ends than at its middle or by twisting the tether 2346 tighter at the tether portion 2356.

Although certain embodiments have been shown and described, it is understood that equivalents and modifications falling within the scope of the appended claims will occur to others who are skilled in the art upon the reading and understanding of this specification.

What is claimed is:

1. A ureteral stent for placement in a bladder, a kidney, and a ureteral passageway that connects the bladder and the kidney, the ureteral stent including:
    a solid bladder coil free of a lumen, the sold bladder coil being positionable in the bladder and being buoyant, the solid bladder coil having first and second ends and being movable between a first restrained position during positioning in the bladder and a first unrestrained position after positioning in the bladder preventing migration into the ureteral passageway, wherein the solid bladder coil is conical at the second end and includes an eyelet at the first end;
    a tubular kidney member positionable in the kidney and the ureteral passageway, the tubular kidney member having a ureter portion configured to be positioned in the kidney and the ureteral passageway to place the ureteral passageway in an open state, and a resilient fixing portion movable between a second restrained position during positioning in the kidney and a second unrestrained position after positioning in the kidney to retain the resilient fixing portion in the kidney; and
    a tether connecting the solid bladder coil and the ureter portion to allow the solid bladder coil to float in the bladder and to allow a ureter orifice connecting the ureteral passageway to the bladder to move between a compressed state and an uncompressed state,
    wherein the tether is received in an opening of the ureter portion such that a first portion of the tether is outside the ureter portion and a second portion of the tether is inside the ureter portion, and wherein the tether has first and second ends coupled to the second end of the solid bladder coil at an outer portion thereof,
    wherein the first and second ends of the tether are coupled to the solid bladder coil by melting the first and second ends of the tether to the second end of the solid bladder coil, and
    wherein the eyelet is configured to receive a removal tether for removing the ureteral stent from a patient.

2. The ureteral stent according to claim 1, wherein the solid bladder coil has a diameter in a range of 0.025 inches to 0.050 inches to allow the solid bladder coil to be inserted into the bladder alongside a stent pusher.

3. The ureteral stent according to claim 2, wherein the solid bladder coil has a diameter less than or equal to 0.035 inches.

4. The ureteral stent according to claim 1, wherein the solid bladder coil includes a radiopaque filler.

5. A ureteral stent for placement in a bladder, a kidney, and a ureteral passageway that connects the bladder and the kidney, the ureteral stent including:

a solid bladder member free of a lumen and having first and second terminal ends, the solid bladder member being positionable in the bladder;

a tubular kidney member positionable in the kidney and the ureteral passageway to place the ureteral passageway in an open state and to secure the stent in the kidney, the tubular kidney member having a lumen and an opening in a wall of the kidney member into the lumen; and a tether connecting the solid bladder member and the kidney member to allow the solid bladder member to float in the bladder and to allow a ureter orifice connecting the ureteral passageway to the bladder to move between a compressed state and an uncompressed state, wherein the tether is received in the opening of the kidney member such that the tether extends through the lumen and outside the kidney member, and wherein the tether has first and second ends affixed to an outer surface of the solid bladder member at the second terminal end of the solid bladder member, and wherein the first and second ends of the tether are affixed to the solid bladder member by melting the first and second ends of the tether and the second end of the solid bladder member.

6. The ureteral stent according to claim 5, wherein the solid bladder member has an eyelet at the first terminal end, the eylet being configured to receive a removal tether for removing the ureteral stent from a patient.

7. The ureteral stent according to claim 5, wherein the solid bladder member has a diameter in a range of 0.025 inches to 0.050 inches to allow the solid bladder member to be inserted into the bladder alongside a stent pusher.

8. The ureteral stent according to claim 7, wherein the solid bladder member has a diameter less than or equal to 0.035 inches.

9. The ureteral stent according to claim 5, wherein the solid bladder member is a solid coil, and wherein the solid coil is movable between a restrained position during positioning in the bladder and an unrestrained position after positioning in the bladder preventing migration into the ureteral passageway.

10. The ureteral stent according to claim 5, wherein the tether is affixed to the outer surface of the solid bladder member at the second terminal end by a process whereby the first and second ends of the tether and the second terminal end of the solid bladder member are melted together.

11. A ureteral stent for placement in a bladder, a kidney, and a ureteral passageway that connects the bladder and the kidney, the ureteral stent including:

a solid bladder member free of a lumen and having first and second terminal ends and an eyelet formed at the first end, the solid bladder member being positionable in the bladder and being formed of a material allowing the solid bladder member to be moved between a restrained position during positioning in the bladder and an unrestrained position after positioning in the bladder preventing migration into the ureteral passageway;

a tubular kidney member positionable in the kidney and the ureteral passageway to place the ureteral passageway in an open state and to secure the stent in the kidney, the tubular kidney member having a lumen and an opening in a wall of the kidney member into the lumen; and a tether connecting the solid bladder member and the kidney member to allow the solid bladder member to float in the bladder and to allow a ureter orifice connecting the ureteral passageway to the bladder to move between a compressed state and an uncompressed state, wherein the tether is received in the opening of the kidney member such that the tether extends through the lumen and outside the kidney member, and wherein the tether has first and second ends affixed to an outer surface of the solid bladder member at the second terminal end of the solid bladder member, and wherein the first and second ends of the tether are affixed to the solid bladder member by melting the first and second ends of the tether and the second end of the solid bladder member.

12. The ureteral stent according to claim 11, wherein the solid bladder member has a diameter less than or equal to about 0.035 inches to allow the solid bladder member to be introduced into the bladder alongside a stent pusher.

* * * * *